US006177455B1

(12) United States Patent
Steiner et al.

(10) Patent No.: US 6,177,455 B1
(45) Date of Patent: *Jan. 23, 2001

(54) PYRROLIDINE DERIVATIVE HAIR GROWTH COMPOSITIONS AND USES

(75) Inventors: Joseph P. Steiner, Finksburg; Gregory S. Hamilton, Catonsville, both of MD (US)

(73) Assignee: Gpi Nil Holdings, Inc., Wilmington, DE (US)

( * ) Notice: Under 35 U.S.C. 154(b), the term of this patent shall be extended for 0 days.

This patent is subject to a terminal disclaimer.

(21) Appl. No.: 09/089,415

(22) Filed: Jun. 3, 1998

Related U.S. Application Data

(63) Continuation-in-part of application No. 08/869,426, filed on Jun. 4, 1997, now Pat. No. 5,945,441.

(51) Int. Cl.$^7$ ..................................... A61K 31/40

(52) U.S. Cl. ........................ 514/422; 514/422; 514/880

(58) Field of Search ..................... 514/422, 423

(56) References Cited

U.S. PATENT DOCUMENTS

| | | |
|---|---|---|
| 4,310,461 | 1/1982 | Krapcho et al. . |
| 4,374,829 | 2/1983 | Harris et al. . |
| 4,390,695 | 6/1983 | Krapcho et al. . |
| 4,438,031 | 3/1984 | Winkley et al. . |
| 4,531,964 | 7/1985 | Shimano et al. . |
| 4,574,079 | 3/1986 | Gavras et al. . |
| 4,578,474 | 3/1986 | Krapcho et al. . |
| 4,593,102 | 6/1986 | Shanklin, Jr. . |
| 4,808,573 | 2/1989 | Gold et al. . |
| 4,818,749 | 4/1989 | Gold et al. . |
| 4,996,193 | 2/1991 | Hewitt et al. . |
| 5,147,877 | 9/1992 | Goulet . |
| 5,189,042 | 2/1993 | Goulet et al. . |
| 5,192,773 | 3/1993 | Armistead et al. . |
| 5,208,241 | 5/1993 | Ok et al. . |
| 5,252,579 | 10/1993 | Skotnicki et al. . |
| 5,258,389 | 11/1993 | Goulet et al. . |
| 5,284,826 | 2/1994 | Eberle . |
| 5,284,840 | 2/1994 | Rupprecht et al. . |
| 5,284,877 | 2/1994 | Organ et al. . |
| 5,292,747 | 3/1994 | Davis et al. . |
| 5,294,603 | 3/1994 | Rinehart . |
| 5,319,098 | 6/1994 | Burbaum et al. . |
| 5,330,993 | 7/1994 | Armistead et al. . |
| 5,342,625 | 8/1994 | Hauer et al. . |
| 5,359,138 | 10/1994 | Takeuchi et al. . |
| 5,385,908 | 1/1995 | Nelson et al. . |
| 5,385,918 | 1/1995 | Connell et al. . |
| 5,414,083 | 5/1995 | Hackl et al. . |
| 5,424,454 | 6/1995 | Burbaum et al. . |
| 5,447,915 | 9/1995 | Schreiber et al. . |
| 5,457,111 | 10/1995 | Luly et al. . |
| 5,470,878 | 11/1995 | Michnick et al. . |
| 5,472,687 | 12/1995 | Proctor . |
| 5,506,228 | 4/1996 | Norton et al. . |
| 5,516,797 | 5/1996 | Armistead et al. . |
| 5,532,248 | 7/1996 | Goulet et al. . |
| 5,543,423 | 8/1996 | Zelle et al. . |
| 5,614,547 | 3/1997 | Hamilton et al. . |
| 5,620,971 | 4/1997 | Armistead et al. . |
| 5,631,017 | 5/1997 | Sharpe et al. . |
| 5,703,088 | 12/1997 | Sharpe et al. . |
| 5,714,510 | 2/1998 | Proctor . |

FOREIGN PATENT DOCUMENTS

| | | |
|---|---|---|
| 2505114 | 8/1976 | (DE) . |
| 3508251 | 9/1986 | (DE) . |
| 3931051 | 3/1990 | (DE) . |
| 4015255 | 11/1991 | (DE) . |
| 12401 | 6/1980 | (EP) . |
| 48159 | 3/1982 | (EP) . |
| 50800 | 5/1982 | (EP) . |
| 73143 | 3/1983 | (EP) . |
| 88350 | 9/1983 | (EP) . |
| 196841 | 10/1986 | (EP) . |
| 260118 | 3/1988 | (EP) . |
| 333174 | 9/1989 | (EP) . |
| 352000 | 1/1990 | (EP) . |
| 378318 | 7/1990 | (EP) . |
| 0420707 | 8/1990 | (EP) . |
| 0471135 | 8/1990 | (EP) . |
| 405994 | 1/1991 | (EP) . |
| 419049 | 3/1991 | (EP) . |
| 423714 | 4/1991 | (EP) . |
| 0443983 | 12/1991 | (EP) . |
| 0494005 | 12/1991 | (EP) . |
| 468339 | 1/1992 | (EP) . |
| 0519819 | 6/1992 | (EP) . |
| 564924 | 10/1993 | (EP) . |
| 572365 | 12/1993 | (EP) . |
| 652229 | 5/1995 | (EP) . |
| 0823419 | 8/1997 | (EP) . |
| 2247456 | 3/1992 | (GB) . |
| 04149166 | 5/1992 | (JP) . |
| 05178824 | 7/1993 | (JP) . |
| WO 8800040 | 1/1988 | (WO) . |
| WO8809789 | 12/1988 | (WO) . |
| WO 8906234 | 7/1989 | (WO) . |
| WO9012805 | 11/1990 | (WO) . |
| WO9104985 | 4/1991 | (WO) . |
| WO9113088 | 9/1991 | (WO) . |
| WO9200278 | 1/1992 | (WO) . |
| WO9203472 | 3/1992 | (WO) . |
| WO9204370 | 3/1992 | (WO) . |
| WO9216501 | 10/1992 | (WO) . |
| WO9218478 | 10/1992 | (WO) . |
| WO9219593 | 11/1992 | (WO) . |
| WO9219745 | 11/1992 | (WO) . |
| WO9221313 | 12/1992 | (WO) . |
| WO9307269 | 4/1993 | (WO) . |
| WO 9314072 | 7/1993 | (WO) . |

(List continued on next page.)

*Primary Examiner*—Rebecca Cook
(74) *Attorney, Agent, or Firm*—Gary M. Nath; Todd L. Juneau; Lee C. Heiman

(57) ABSTRACT

This invention relates to pharmaceutical compositions and methods for treating alopecia and promoting hair growth using pyrrolidine derivatives.

16 Claims, 5 Drawing Sheets

FOREIGN PATENT DOCUMENTS

| | | |
|---|---|---|
| WO9313066 | 7/1993 | (WO). |
| WO 9314762 | 8/1993 | (WO). |
| WO 9318736 | 9/1993 | (WO). |
| WO9323548 | 11/1993 | (WO). |
| WO9325546 | 12/1993 | (WO). |
| WO 9403476 | 2/1994 | (WO). |
| WO9405639 | 3/1994 | (WO). |
| WO9407858 | 4/1994 | (WO). |
| WO9413629 | 6/1994 | (WO). |
| WO 9502684 | 1/1995 | (WO). |
| WO 9512398 | 5/1995 | (WO). |
| WO9512572 | 5/1995 | (WO). |
| WO9524385 | 9/1995 | (WO). |
| WO 9611943 | 10/1995 | (WO). |
| WO9526337 | 10/1995 | (WO). |
| WO 9534303 | 12/1995 | (WO). |
| WO9535308 | 12/1995 | (WO). |
| WO9535367 | 12/1995 | (WO). |
| WO9606097 | 2/1996 | (WO). |
| WO9615101 | 5/1996 | (WO). |
| WO9617816 | 6/1996 | (WO). |
| WO9603318 | 10/1996 | (WO). |
| WO9633184 | 10/1996 | (WO). |
| WO9633187 | 10/1996 | (WO). |
| WO9636630 | 11/1996 | (WO). |
| WO 9641609 | 12/1996 | (WO). |
| WO 9731898 | 9/1997 | (WO). |
| WO 9736869 | 10/1997 | (WO). |
| WO 9813343 | 4/1998 | (WO). |
| WO 9822432 | 5/1998 | (WO). |
| WO9820891 | 5/1998 | (WO). |
| WO9820892 | 5/1998 | (WO). |
| WO9820893 | 5/1998 | (WO). |
| WO9824805 | 6/1998 | (WO). |
| 9207782 | 4/1993 | (ZA). |

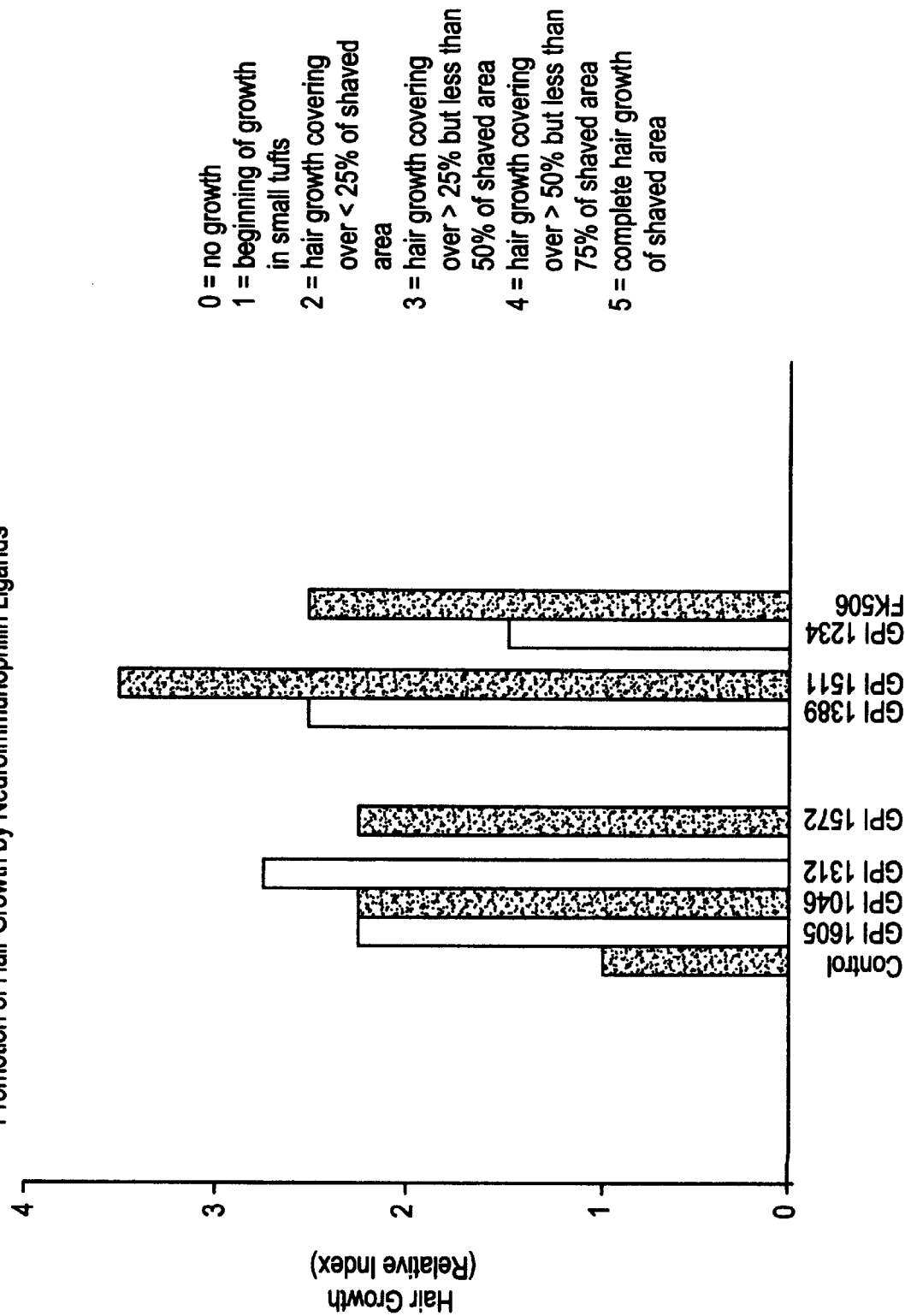

PYRROLIDINE DERIVATIVE HAIR GROWTH COMPOSITIONS AND USES

This application is a continuation-in-part of U.S. patent application Ser. No. 08/869,426, filed on Jun. 4, 1997, now U.S. Pat. No. 5,945,441 the entire contents of which are herein incorporated by reference.

BACKGROUND OF THE INVENTION

1. Field of Invention

This invention relates to pharmaceutical compositions and methods for treating alopecia and promoting hair growth using low molecular weight, small molecule pyrrolidine derivatives.

2. Description of Related Art

Hair loss occurs in a variety of situations. These situations include male pattern alopecia, alopecia senilis, alopecia areata, diseases accompanied by basic skin lesions or tumors, and systematic disorders such as nutritional disorder and internal secretion disorders. The mechanisms causing hair loss are very complicated, but in some instances can be attributed to aging, genetic disposition, the activation of male hormones, the loss of blood supply to hair follicles, and scalp abnormalities.

The immunosuppressant drugs FK506, rapamycin and cyclosporin are well known as potent T-cell specific immunosuppressants, and are effective against graft rejection after organ transplantation. It has been reported that topical, but not oral, application of FK506 (Yamamoto et al., J. Invest. Dermatol., 1994, 102, 160–164; Jiang et al., J. Invest. Dermatol. 1995, 104, 523–525) and cyclosporin (Iwabuchi et al., J. Dermatol. Sci. 1995, 9, 64–69) stimulates hair growth in a dose-dependent manner. One form of hair loss, alopecia areata, is known to be associated with autoimmune activities; hence, topically administered immuno-modulatory compounds are expected to demonstrate efficacy for treating that type of hair loss. The hair growth stimulating effects of FK506 have been the subject of an international patent filing covering FK506 and structures related thereto for hair growth stimulation (Honbo et al., EP 0 423 714 A2). Honbo et al. discloses the use of relatively large tricyclic compounds, known for their immunosuppressive effects, as hair revitalizing agents.

The hair growth and revitalization effects of FK506 and related agents are disclosed in many U.S. patents (Goulet et al., U.S. Pat. No. 5,258,389; Luly et al., U.S. Pat. No. 5,457,111; Goulet et al., U.S. Pat. No. 5,532,248; Goulet et al., U.S. Pat. No. 5,189,042; and Ok et al., U.S. Pat. No. 5,208,241; Rupprecht et al., U.S. Pat. No. 5,284,840; Organ et al., U.S. Pat. No. 5,284,877). These patents claim FK506 related compounds. Although they do not claim methods of hair revitalization, they disclose the known use of FK506 for effecting hair growth. Similar to FK506 (and the claimed variations in the Honbo et al. patent), the compounds claimed in these patents are relatively large. Further, the cited patents relate to immunomodulatory compounds for use in autoimmune related diseases, for which FK506's efficacy is well known.

Other U.S. patents disclose the use of cyclosporin and related compounds for hair revitalization (Hauer et al., U.S. Pat. No. 5,342,625; Eberle, U.S. Pat. No. 5,284,826; Hewitt et al., U.S. Pat. No. 4,996,193). These patents also relate to compounds useful for treating autoimmune diseases and cite the known use of cyclosporin and related immunosuppressive compounds for hair growth.

However, immunosuppressive compounds by definition suppress the immune system and also exhibit other toxic side effects. Accordingly, there is a need for non-immunosuppressant, small molecule compounds which are useful as hair revitalizing compounds.

Hamilton and Steiner disclose in U.S. Pat. No. 5,614,547 novel pyrrolidine carboxylate compounds which bind to the immunophilin FKBP12 and stimulate nerve growth, but which lack immunosuppressive effects. Unexpectedly, it has been discovered that these non-immunosuppressant compounds promote hair growth with an efficacy similar to FK506. Yet their novel small molecule structure and non-immunosuppressive properties differentiate them from FK506 and related immunosuppressive compounds found in the prior art.

SUMMARY OF THE INVENTION

The present invention relates to a method for treating alopecia or promoting hair growth in an animal, which comprises administering to said animal an effective amount of a pyrrolidine derivative.

The present invention further relates to a pharmaceutical composition which comprises:

(i) an effective amount of a pyrrolidine derivative for treating alopecia or promoting hair growth in an animal; and (ii) a pharmaceutically acceptable carrier.

The pyrrolidine derivatives used in the inventive methods and pharmaceutical compositions have an affinity for FKBP-type immunophilins and do not any significant immunosuppressive activity.

BRIEF DESCRIPTION OF THE DRAWINGS

FIG. 2 shows that less than 3% of the shaved area is covered with new hair growth when the vehicle (control) is administered.

FIG. 3 shows the remarkable effects of non-immunosuppressive neuro-immunophilin FKBP ligands, wherein 90% of the shaved area is covered with new hair growth.

FIG. 4 shows the remarkable ability of non-immunosuppressive neuroimmunophilin FKBP ligands to achieve, essentially, complete hair regrowth in the shaved area.

FIG. 5 is a bar graph depicting the relative hair growth indices for C57 Black 6 mice treated with a vehicle, FK506, and various non-immunosuppressive neuroimmunophilin FKBP ligands, including GPI 1046, 14 days after treatment with each identified compound. FIG. 5 demonstrates the remarkable early hair growth promoted by a wide variety of non-immunosuppressive neuroimmunophilin FKBP ligands.

DETAILED DESCRIPTION OF THE INVENTION

Definitions

Figure 1:
FIG. 1 is a photograph of C57 Black 6 mice before being shaved for the hair regeneration experiment.

"Alopecia" refers to deficient hair growth and partial or complete loss of hair, including without limitation androgenic alopecia (male pattern baldness), toxic alopecia, alopecia senilis, alopecia areata, alopecia pelada and trichotillomania. Alopecia results when the pilar cycle is disturbed. The most frequent phenomenon is a shortening of the hair growth or anagen phase due to cessation of cell proliferation. This results in an early onset of the catagen phase, and consequently a large number of hairs in the telogen phase during which the follicles are detached from the dermal papillae, and the hairs fall out. Alopecia has a number of etiologies, including genetic factors, aging, local and systemic diseases, febrile conditions, mental stresses, hormonal problems, and secondary effects of drugs.

"GPI 1605" refers to a compound of formula

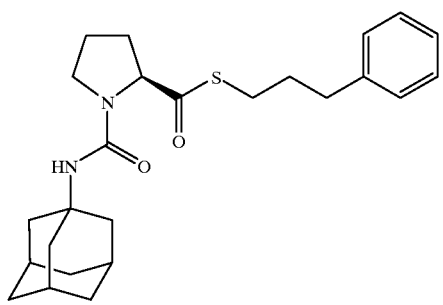

GPI 1605

"GPI 1046" refers to 3-(3-pyridyl)-1-propyl (2s)-1-(3,3-dimethyl-1,2-dioxopentyl)-2-pyrrolidinecarboxylate, a compound of formula

GPI 1046

"GPI 1312" refers to a compound of formula

GPI 1312

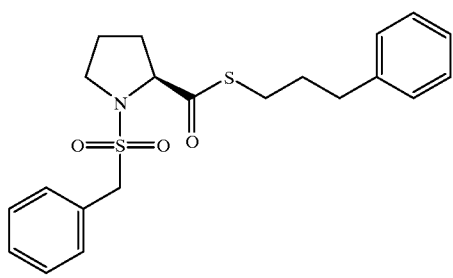

"GPI 1572" refers to a compound of formula

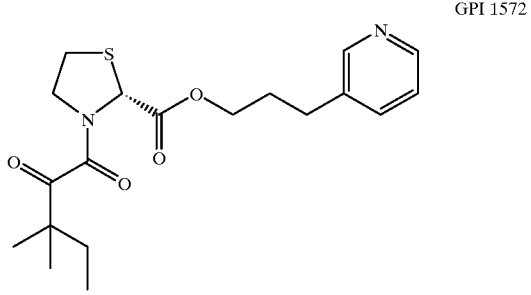

GPI 1572

"GPI 1389" refers to a compound of formula

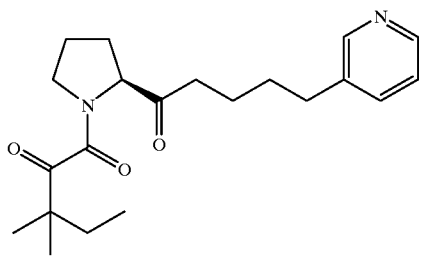

GPI 1389

"GPI 1511" refers to a compound of formula

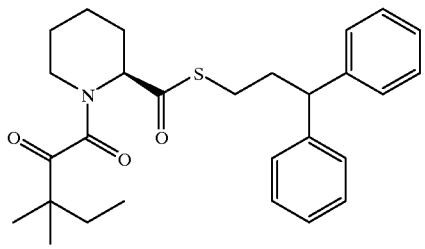

GPI 1511

"GPI 1234" refers to a compound of formula

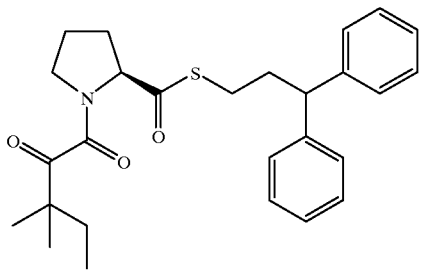

GPI 1234

"Isomers" refer to different compounds that have the same molecular formula. "Stereoisomers" are isomers that differ only in the way the atoms are arranged in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

"Pharmaceutically acceptable salt, ester, or solvate" refers to a salt, ester, or solvate of a subject compound which possesses the desired pharmacological activity and which is neither biologically nor otherwise undesirable. A salt, ester, or solvate can be formed with inorganic acids such as acetate, adipate, alginate, aspartate, benzoate, benzenesulfonate, bisulfate, butyrate, citrate, camphorate, camphorsulfonate, cyclopentanepropionate, digluconate, dodecyisulfate, ethanesulfonate, fumarate, glucoheptanoate, gluconate, glycerophosphate, hemisulfate, heptanoate, hexanoate, hydrochloride, hydrobromide, hydroiodide, 2-hydroxyethanesulfonate, lactate, maleate, methanesulfonate, naphthylate, 2-naphthalenesulfonate, nicotinate, oxalate, sulfate, thiocyanate, tosylate and undecanoate. Examples of base salts, esters, or solvates include ammonium salts; alkali metal salts, such as sodium and potassium salts; alkaline earth metal salts, such as calcium and magnesium salts; salts with organic bases, such as dicyclohexylamine salts; N-methyl-D-glucamine; and salts with amino acids, such as arginine, lysine, and so forth. Also, the basic nitrogen-containing groups can be quarternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; aralkyl halides, such as benzyl and phenethyl bromides; and others. Water or oil-soluble or dispersible products are thereby obtained.

"Pilar cycle" refers to the life cycle of hair follicles, and includes three phases:

(1) the anagen phase, the period of active hair growth which, insofar as scalp hair is concerned, lasts about three to five years;

(2) the catagen phase, the period when growth stops and the follicle atrophies which, insofar as scalp hair is concerned, lasts about one to two weeks; and (3) the telogen phase, the rest period when hair progressively separates and finally falls out which, insofar as scalp hair is concerned, lasts about three to four months.

Normally 80 to 90 percent of the follicles are in the anagen phase, less than 1 percent being in the catagen phase, and the rest being in the telogen phase. In the telogen phase, hair is uniform in diameter with a slightly bulbous, non-pigmented root. By contrast, in the anagen phase, hair has a large colored bulb at its root.

"Promoting hair growth" refers to maintaining, inducing, stimulating, accelerating, or revitalizing the germination of hair.

"Treating alopecia" refers to:

(i) preventing alopecia in an animal which may be pre-disposed to alopecia; and/or (ii) inhibiting, retarding or reducing alopecia; and/or (iii) promoting hair growth; and/or (iv) prolonging the anagen phase of the hair cycle; and/or (v) converting vellus hair to growth as terminal hair. Terminal hair is coarse, pigmented, long hair in which the bulb of the hair follicle is seated deep in the dermis. Vellus hair, on the other hand, is fine, thin, non-pigmented short hair in which the hair bulb is located superficially in the dermis. As alopecia progresses, the hairs change from the terminal to the vellus type.

METHODS OF THE PRESENT INVENTION

The present invention relates to a method for treating alopecia or promoting hair growth in an animal, which comprises administering to said animal an effective amount of a pyrrolidine derivative.

The inventive method is particularly useful for treating male pattern alopecia, alopecia senilis, alopecia areata, alopecia resulting from skin lesions or tumors, alopecia resulting from cancer therapy such as chemotherapy and radiation, and alopecia resulting from systematic disorders such as nutritional disorders and internal secretion disorders.

Pharmaceutical Compositions of the Present Invention

The present invention also relates to a pharmaceutical composition comprising:

(i) an effective amount of a pyrrolidine derivative for treating alopecia or promoting hair growth in an animal; and (ii) a pharmaceutically acceptable carrier.

PYRROLIDINE DERIVATIVES

The pyrrolidine derivatives used in the methods and pharmaceutical compositions of the present invention are low molecular weight, small molecule compounds having an affinity for an FKBP-type immunophilins, such as FKBP12. When a pyrrolidine derivative binds to an FKBP-type immunophilin, it has been found to inhibit the prolyl-peptidyl cis-trans isomerase, or rotamase, activity of the binding protein. Unexpectedly, these compounds have also been found to stimulate hair growth. The compounds are devoid of any significant immunosuppressive activity.

FORMULA I

The pyrrolidine derivative may be a compound of formula I

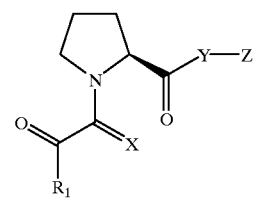

or a pharmaceutically acceptable salt, ester, or solvate thereof, wherein:

$R_1$ is $C_1$–$C_9$ straight or branched chain alkyl, $C_2$–$C_9$ straight or branched chain alkenyl, $C_3$–$C_8$ cycloalkyl, $C_5$–$C_7$ cycloalkenyl or $Ar_1$, wherein said $R_1$ is unsubstituted or substituted with one or more substituents independently seleceted from the group consisting of $C_1$–$C_6$ alkyl, $C_2$–$C_6$ alkenyl, $C_3$–$C_8$ cycloalkyl, $C_5$–$C_7$ cycloalkenyl, hydroxy, and $Ar_2$;

$Ar_1$ and $Ar_2$ are independently selected from the group consisting of 1-napthyl, 2-napthyl, 2-indolyl, 3-indolyl, 2-furyl, 3-furyl, 2-thienyl, 3-thienyl, 2-pyridyl, 3-pyridyl, 4-pyridyl and phenyl, wherein said $Ar_1$ is unsubstituted or substituted with one or more substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and amino;

X is O, S, $CH_2$ or $H_2$;

Y is O or $NR_2$, wherein $R_2$ is hydrogen or $C_1$–$C_6$ alkyl; and

Z is $C_1$–$C_6$ straight or branched chain alkyl, or $C_2$–$C_6$ straight or branched chain alkenyl, wherein said Z is substituted with one or more substituent(s) independently selected from the group consisting of $Ar_1$, $C_3$–$C_8$ cycloalkyl, and $C_1$–$C_6$ straight or branched chain alkyl or $C_2$–$C_6$ straight or branched chain alkenyl substituted with $C_3$–$C_8$ cycloalkyl; or Z is fragment

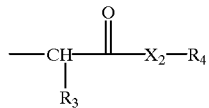

wherein:

$R_3$ is $C_1$–$C_9$ straight or branched chain alkyl which is unsubstituted or substituted with $C_3$–$C_8$ cycloalkyl or $Ar_1$;

$X_2$ is O or $NR_5$, wherein $R_5$ is selected from the group consisting of hydrogen, $C_1$–$C_6$ straight or branched chain alkyl, and $C_2$–$C_6$ straight or branched chain alkenyl; and $R_4$ is selected from the group consisting of phenyl, benzyl, $C_1$–$C_5$ straight or branched chain alkyl, $C_2$–$C_5$ straight or branched chain alkenyl, $C_1$–$C_5$ straight or branched chain alkyl substituted with phenyl, and $C_2$–$C_5$ straight or branched chain alkenyl substituted with phenyl.

In a preferred embodiment of formula I, Z and $R_1$ are lipophilic.

In a more preferred embodiment of formula I, the compound is selected from the group consisting of:

3-phenyl-1-propyl (2S)-1-(3,3-dimethyl-1,2-dioxopentyl)-2-pyrrolidinecarboxylate;

3-phenyl-1-prop-2-(E)-enyl (2S)-1-(3,3-dimethyl-1,2-dioxopentyl)-2-pyrrolidinecarboxylate;

3-(3,4,5-trimethoxyphenyl)-1-propyl (2S)-1-(3,3-dimethyl-1, 2-dioxopentyl)-2-pyrrolidinecarboxylate;

3-(3,4,5-trimethoxyphenyl)-1-prop-2-(E)-enyl (2S)-1-(3,3-dimethyl-1,2-dioxopentyl)-2-pyrrolidinecarboxylate;

3-(4,5-dichlorophenyl)-1-propyl (2S)-1-(3,3-dimethyl-1, 2-dioxopentyl)-2-pyrrolidinecarboxylate;

3-(4,5-dichlorophenyl)-1-prop-2-(E)-enyl (2S)-1-(3,3-dimethyl-1,2-dioxopentyl)-2-pyrrolidinecarboxylate;

3-(4,5-methylenedioxyphenyl)-1-propyl (2S)-1-(3,3-dimethyl-1,2-dioxopentyl)-2-pyrrolidinecarboxylate;

3-(4,5-methylenedioxyphenyl)-1-prop-2-(E)-enyl (2S)-1-(3,3-dimethyl-1,2-dioxopentyl)-2-pyrrolidinecarboxylate;

3-cyclohexyl-1-propyl (2S)-1-(3,3-dimethyl-1,2-dioxopentyl)-2-pyrrolidinecarboxylate;

3-cyclohexyl-1-prop-2-(E)-enyl (2S)-1-(3,3-dimethyl-1, 2-dioxopentyl)-2-pyrrolidinecarboxylate;

(1R)-1,3-diphenyl-1-propyl (2S)-1-(3,3-dimethyl-1,2 -dioxopentyl)-2-pyrrolidlnecarboxylate;

(1R)-1,3-diphenyl-1-prop-2-(E)-enyl (2S)-1-(3,3-dimethyl-1,2-dioxopentyl)-2-pyrrolidinecarboxylate;

(1R)-1-cyclohexyl-3-phenyl-1-propyl (2S)-1-(3,3-dimethyl-1,2-dioxopentyl)-2-pyrrolidinecarboxylate;

(1R) -1-cyclohexyl-3-phenyl-1-prop-2-(E)-enyl (2S)-1-(3,3-dimethyl-1,2-dioxopentyl)-2-pyrrolidinecarboxylate;

(1R)-1-(4,5-dichlorophenyl)-3-phenyl-1-propyl (2S)-1-(3,3-dimethyl-1,2-dioxopentyl)-2-pyrrolidinecarboxylate;

3-phenyl-1-propyl (2S)-1-(1,2-dioxo-2-cyclohexyl)ethyl-2-pyrrolidinecarboxylate;

3-phenyl-1-propyl (2S)-1-(1,2-dioxo-4-cyclohexyl)butyl-2-pyrrolidinecarboxylate;

3-phenyl-1-propyl (2S)-1-1,2-dioxo-2-[2-furanyl])ethyl-2-pyrrolidinecarboxylate;

3-phenyl-1-propyl (2S)-1-(1,2-dioxo-2-[2-thienyl])ethyl-2-pyrrolidinecarboxylate;

3-phenyl-1-propyl (2S)-1-(1,2-dioxo-2-[2-thiazolyl])ethyl-2-pyrrolidinecarboxylate;

3-phenyl-1-propyl (2S)-1-(1,2-dioxo-2-phenyl)ethyl-2-pyrrolidinecarboxylate;

1,7-diphenyl-4-heptyl (2S)-1-(3,3-dimethyl-1,2-dioxopentyl)-2-pyrrolidinecarboxylate;

3-phenyl-1-propyl (2S)-1-(3,3-dimethyl-1,2-dioxo-4-hydroxybutyl)-2-pyrrolidinecarboxylate;

3-phenyl-1-propyl (2S)-1-(3,3-dimethyl-1,2-dioxopentyl)-2-pyrrolidinecarboxamide;

1-[1-(3,3-dimethyl-1,2-dioxopentyl)-L-proline]-L-phenylalanine ethyl ester;

1-[1-(3,3-dimethyl-1,2-dioxopentyl)-L-proline]-L-leucine ethyl ester;

1-[1-(3,3-dimethyl-1,2-dioxopentyl)-L-proline]-L-phenylglycine ethyl ester;

1-[1-(3,3-dimethyl-1,2-dioxopentyl)-L-proline]-L-phenylalanine phenyl ester;

1-[1-(3,3-dimethyl-1,2-dioxopentyl)-L-proline]-L-phenylalanine benzyl ester;

1-[1-(3,3-dimethyl-1,2-dioxopentyl)-L-proline]-L-isoleucine ethyl ester; and pharmaceutically acceptable salts, esters, and solvates thereof.

FORMULA II

The pyrrolidine derivative may also be a compound of formula II

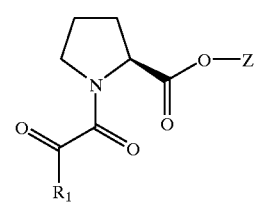

or a pharmaceutically acceptable salt, ester, or solvate thereof, wherein:

$R_1$ is $C_1$–$C_9$ straight or branched chain alkyl, $C_2$–$C_9$ straight or branched chain alkenyl, $C_3$–$C_8$ cycloalkyl, $C_{5-C7}$ cycloalkenyl or $Ar_1$, wherein said $R_1$ is unsubstituted or substituted with one or more substituents independently seleceted from the group consisting of $C_1$–$C_6$ alkyl, $C_2$–C6 alkenyl, $C_3$–$C_8$ cycloalkyl, $C_5$–$C_7$ cycloalkenyl, hydroxy, and $Ar_2$;

$Ar_1$ and $Ar_2$ are independently selected from the group consisting of 1-napthyl, 2-napthyl, 2-indolyl, 3-indolyl, 2-furyl, 3-furyl, 2-thienyl, 3-thienyl, 2-pyridyl, 3-pyridyl, 4-pyridyl and phenyl, wherein said $Ar_1$ is unsubstituted or substituted with one or more substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and amino;

Z is $C_1$–$C_6$ straight or branched chain alkyl, or $C_2$–$C_6$ straight or branched chain alkenyl, wherein said Z is substituted with one or more substituent(s) independently selected from the group consisting of $Ar_1$, $C_3$–$C_8$ cycloalkyl, and $C_1$–$C_6$ straight or branched chain alkyl or $C_2$–$C_6$ straight or branched chain alkenyl substituted with $C_3$–$C_8$ cycloalkyl; or Z is fragment

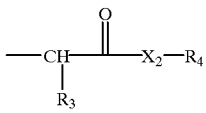

wherein:
$R_3$ is $C_1$–$C_9$ straight or branched chain alkyl which is unsubstituted or substituted with $C_3$–$C_8$ cycloalkyl or $Ar_1$;
$X_2$ is O or $NR_5$, wherein $R_5$ is selected from the group consisting of hydrogen, $C_1$–$C_6$ straight or branched chain alkyl, and $C_2$–$C_6$ straight or branched chain alkenyl; and
$R_4$ is selected from the group consisting of phenyl, benzyl, $C_1$–$C_5$ straight or branched chain alkyl, $C_2$–$C_5$ straight or branched chain alkenyl, $C_1$–$C_5$ straight or branched chain alkyl substituted with phenyl, and $C_2$–$C_5$ straight or branched chain alkenyl substituted with phenyl.

In a preferred embodiment of formula II, $R_1$ is selected from the group consisting of $C_1$–$C_9$ straight or branched chain alkyl, 2-cyclohexyl, 4-cyclohexyl, 2-furanyl, 2-thienyl, 2-thiazolyl, and 4-hydroxybutyl.

In another preferred embodiment of formula II, Z and $R_1$ are lipophilic.

FORMULA III

The pyrrolidine derivative may also be a compound of formula III

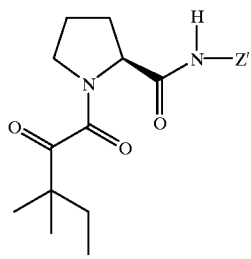

or a pharmaceutically acceptable salt, ester, or solvate thereof, wherein:
Z' is fragment

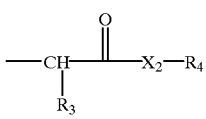

wherein:
$R_3$ is $C_1$–$C_9$ straight or branched chain alkyl or unsubstituted $Ar_1$, wherein said alkyl is unsubstituted or substituted with $C_3$–$C_8$ cycloalkyl or $Ar_1$;
$X_2$ is O or $NR_5$, wherein $R_5$ is selected from the group consisting of hydrogen, $C_1$–$C_6$ straight or branched chain alkyl, and $C_2$–$C_6$ straight or branched chain alkenyl;
$R_4$ is selected from the group consisting of phenyl, benzyl, $C_1$–$C_5$ straight or branched chain alkyl, $C_2$–$C_5$ straight or branched chain alkenyl, $C_1$–$C_5$ straight or branched chain alkyl substituted with phenyl, and $C_2$–$C_5$ straight or branched chain alkenyl substituted with phenyl; and
$Ar_1$ is as defined in formula II.

In a preferred embodiment of formula III, Z' is lipophilic.

FORMULA IV

Additionally, the pyrrolidine derivative may be a compound of formula IV

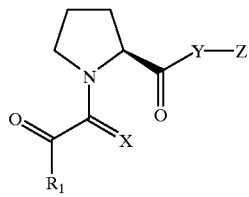

wherein:
$R_1$ is $C_1$–$C_6$ straight or branched chain alkyl, $C_2$–$C_6$ straight or branched chain alkenyl, $C_3$–$C_6$ cycloalkyl or $Ar_1$, wherein said alkyl or alkenyl is unsubstituted or substituted with $C_3$–$C_6$ cycloalkyl or $Ar_2$;
$Ar_1$ and $Ar_2$ are independently selected from the group consisting of 2-furyl, 2-thienyl, and phenyl;
X is selected from the group consisting of oxygen and sulfur;
Y is oxygen;
Z is $C_1$–$C_6$ straight or branched chain alkyl, or $C_2$–$C_6$ straight or branched chain alkenyl, wherein said Z is substituted with one or more substituent(s) independently selected from the group consisting of 2-furyl, 2-thienyl, $C_3$–$C_6$ cycloalkyl, pyridyl, and phenyl, each having one or more substituent(s) independently selected from the group consisting of hydrogen and $C_1$–$C_4$ alkoxy.

In a preferred embodiment of formula IV, Z and $R_1$ are lipophilic.

In another preferred embodiment of formula IV, the compound is selected from the group consisting of:
3-(2,5-dimethoxyphenyl)-1-propyl (2S)-1-(3,3-dimethyl-1,2-dioxopentyl)-2-pyrrolidinecarboxylate;
3-(2,5-dimethoxyphenyl)-1-prop-2-(E)-enyl (2S)-1-(3,3-dimethyl-1,2-dioxopentyl)-2-pyrrolidinecarboxylate;
2-(3,4,5-trimethoxyphenyl)-1-ethyl (2S)-1-(3,3-dimethyl-1,2-dioxopentyl)-2-pyrrolidinecarboxylate;
3-(3-pyridyl)-1-propyl (2S)-1-(3,3-dimethyl-1,2-dioxopentyl)-2-pyrrolidinecarboxylate;
3-(2-pyridyl)-1-propyl (2S)-1-(3,3-dimethyl-1,2-dioxopentyl)-2-pyrrolidinecarboxylate;
3-(4-pyridyl)-1-propyl (2S)-1-(3,3-dimethyl-1,2-dioxopentyl)-2-pyrrolidinecarboxylate;
3-phenyl-1-propyl (2S)-1-(2-tert-butyl-1,2-dioxoethyl)-2-pyrrolidinecarboxylate;
3-phenyl-1-propyl (2S)-1-(2-cyclohexylethyl-1,2-dioxoethyl)-2-pyrrolidinecarboxylate;
3-(3-pyridyl)-1-propyl (2S)-1-(2-cyclohexylethyl-1,2-dioxoethyl)-2-pyrrolidinecarboxylate;
3-(3-pyridyl)-1-propyl (2S)-1-(2-tert-butyl-1,2-dioxoethyl)-2-pyrrolidinecarboxylate;
3,3-diphenyl-1-propyl (2S)-1-(3,3-dimethyl-1,2-dioxopentyl)-2-pyrrolidinecarboxylate;
3-(3-pyridyl)-1-propyl (2S)-1-(2-cyclohexyl-1,2-dioxoethyl)-2-pyrrolidinecarboxylate;
3-(3-pyridyl)-1-propyl (2S)-N-([2-thienyl]glyoxyl) pyrrolidinecarboxylate;
3,3-diphenyl-1-propyl (2S)-1-(3,3-dimethyl-1,2-dioxobutyl)-2-pyrrolidinecarboxylate;
3,3-diphenyl-1-propyl (2S)-1-cyclohexylglyoxyl-2-pyrrolidinecarboxylate;
3,3-diphenyl-1-propyl (2S)-1-(2-thienyl)glyoxyl-2-pyrrolidinecarboxylate; and
pharmaceutically acceptable salts, esters, and solvates thereof.

In a more preferred embodiment of formula IV, the compound is selected from the group consisting of:

3-(3-pyridyl)-1-propyl (2S)-1-(3,3-dimethyl-1,2-dioxopentyl)-2-pyrrolidinecarboxylate;

3-(2-pyridyl)-1-propyl (2S)-1-(3,3-dimethyl-1,2-dioxopentyl)-2-pyrrolidinecarboxylate;

3-(3-pyridyl)-1-propyl (2S)-1-(2-cyclohexyl-1,2-dioxoethyl)-2-pyrrolidinecarboxylate; and pharmaceutically acceptable salts, esters, and solvates thereof.

In the most preferred embodiment of formula IV, the compound is 3-(3-pyridyl)-1-propyl (2S)-1-(3,3-dimethyl-1,2-dioxopentyl)-2-pyrrolidinecarboxylate, and pharmaceutically acceptable salts, esters, and solvates thereof.

FORMULA V

Additionally, the pyrrolidine derivative may be a compound of formula V

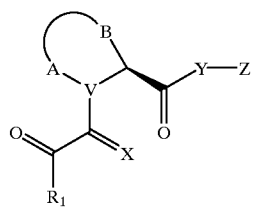

or a pharmaceutically acceptable salt, ester, or solvate thereof, wherein:

V is C, N, or S;

A and B, taken together with V and the carbon atom to which they are respectively attached, form a 5–7 membered saturated or unsaturated heterocyclic ring containing, in addition to V, one or more heteroatom(s) selected from the group consisting of O, S, SO, $SO_2$, N, NH, and NR;

R is either $C_1-C_9$ straight or branched chain alkyl, $C_2-C_9$ straight or branched chain alkenyl, $C_3-C_9$ cycloalkyl, $C_5-C_7$ cycloalkenyl, or $Ar_1$, wherein R is either unsubstituted of substituted with one or more substituent(s) independently selected from the group consisting of halo, haloalkyl, carbonyl, carboxy, hydroxy, nitro, trifluoromethyl, $C_1-C_6$ straight or branched chain alkyl, $C_2-C_6$ straight or branched chain alkenyl, $C_1-C_4$ alkoxy, $C_2-C_4$ alkenyloxy, phenoxy, benzyloxy, thioalkyl, alkylthio, sulfhydryl, amino, alkylamino, aminoalkyl, aminocarboxyl, and $Ar_2$;

$R_1$ is $C_1-C_9$ straight or branched chain alkyl, $C_2-C_9$ straight or branched chain alkenyl, $C_3-C_8$ cycloalkyl, $C_5-C_7$ cycloalkenyl or $Ar_1$, wherein said $R_1$ is unsubstituted or substituted with one or more substituents independently seleceted from the group consisting of $C_1-C_6$ alkyl, $C_2-C_6$ alkenyl, $C_3-C_8$ cycloalkyl, $C_5-C_7$ cycloalkenyl, hydroxy, and $Ar_2$;

$Ar_1$ and $Ar_2$ are independently an alicyclic or aromatic, mono-, bi- or tricyclic, carbo- or heterocyclic ring, wherein the ring is either unsubstituted or substituted with one or more substituent(s); wherein the individual ring size is 5–8 members; wherein said heterocyclic ring contains 1–6 heteroatom(s) independently selected from the group consisting of O, N, and S;

X is O, S, $CH_2$ or $H_2$;

Y is O or $NR_2$, wherein $R_2$ is hydrogen or $C_1-C_6$ alkyl; and

Z is $C_1-C_6$ straight or branched chain alkyl, or $C_2-C_6$ straight or branched chain alkenyl, wherein said Z is substituted with one or more substituent(s) independently selected from the group consisting of $Ar_1$, $C_3-C_8$ cycloalkyl, and $C_1-C_6$ straight or branched chain alkyl or $C_2-C_6$ straight or branched chain alkenyl substituted with $C_3-C_8$ cycloalkyl; or Z is fragment

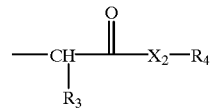

wherein:

$R_3$ is $C_1-C_9$ straight or branched chain alkyl which is unsubstituted or substituted with $C_3-C_8$ cycloalkyl or $Ar_1$;

$X_2$ is O or $NR_5$, wherein $R_5$ is selected from the group consisting of hydrogen, $C_1-C_6$ straight or branched chain alkyl, and $C_2-C_6$ straight or branched chain alkenyl; and $R_4$ is selected from the group consisting of phenyl, benzyl, $C_3-C_5$ straight or branched chain alkyl, $C_2-C_5$ straight or branched chain alkenyl, $C_1-C_5$ straight or branched chain alkyl substituted with phenyl, and $C_2-C_5$ straight or branched chain alkenyl substituted with phenyl.

All the compounds of Formulas I–V possess asymmetric centers and thus can be produced as mixtures of stereoisomers or as individual R- and S-stereoisomers. The individual stereoisomers may be obtained by using an optically active starting material, by resolving a racemic or non-racemic mixture of an intermediate at some appropriate stage of the synthesis, or by resolving the compounds of Formulas I–V. It is understood that the compounds of Formulas I–V encompass individual stereoisomers as well as mixtures (racemic and non-racemic) of stereoisomers. Preferably, S-stereoisomers are used in the pharmaceutical compositions and methods of the present invention.

Synthesis of Pyrrolidine Derivatives

The compounds of formulas I to V may be prepared by a variety of synthetic sequences that utilize established chemical transformations. The general pathway to the present compounds is described in Scheme I. N-glyoxylproline derivatives may be prepared by reacting L-proline methyl ester with methyl oxalyl chloride as shown in Scheme I. The resulting oxamates may be reacted with a variety of carbon nucleophiles to obtain intermediate compounds. These intermediates are then reacted with a variety of alcohols, amides, or protected amino acid residues to obtain the propyl esters and amides of the invention.

SCHEME I

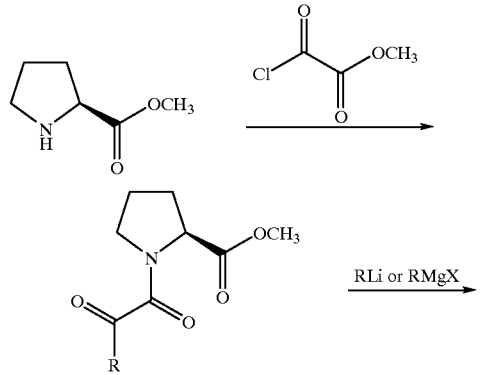

-continued

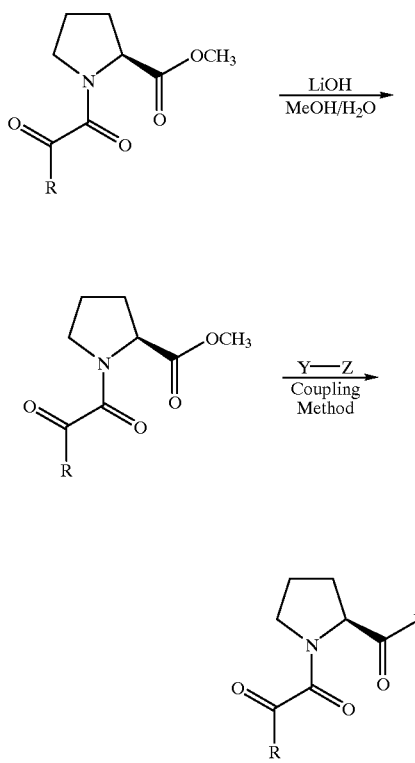

The substituted alcohols may be prepared by a number of methods known to those skilled in the art of organic synthesis. As described in Scheme II, alkyl or aryl aldehydes may be homologated to phenyl propanols by reaction with methyl(triphenylphosphoranylidene)acetate to provide a variety of trans-cinnamates; these latter may be reduced to the saturated alcohols by reaction with excess lithium aluminum hydride, or sequentially by reduction of the double bond by catalytic hydrogenation and reduction of the saturated ester by appropriate reducing agents. Alternatively, the trans-cinnamates may be reduced to (E)-allylic alcohols by the use of diisobutylaluminum hydride.

Longer chain alcohols may be prepared by homologation of benzylic and higher aldehydes. Alternatively, these aldehydes may be prepared by conversion of the corresponding phenylacetic and higher acids, and phenethyl and higher alcohols.

Affinity for FKBP12

The compounds used in the inventive methods and pharmaceutical compositions have an affinity for the FK506 binding protein, particularly FKBP12. The inhibition of the prolyl peptidyl cis-trans isomerase activity of FKBP may be measured as an indicator of this affinity.

$K_i$ Test Procedure

Inhibition of the peptidyl-prolyl isomerase (rotamase) activity of the compounds used in the inventive methods and pharmaceutical compositions can be evaluated by known methods described in the literature (Harding et al., Nature, 1989, 341:758–760; Holt et al. *J. Am. Chem. Soc.*, 115:9923–9938). These values are obtained as apparent $K_i$'s and are presented for representative compounds in TABLE I. The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent $K_i$ values.

In a plastic cuvette are added 950 mL of ice cold assay buffer (25 mM HEPES, pH 7.8, 100 mM NaCl), 10 mL of FKBP (2.5 mM in 10 mM Tris-Cl pH 7.5, 100 mM NaCl, 1 mM dithiothreitol), 25 mL of chymotrypsin (50 mg/ml in 1 mM HCl) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nm versus time is monitored for 90 seconds using a spectrophotometer and the rate constants are determined from the absorbance versus time data files.

SCHEME II

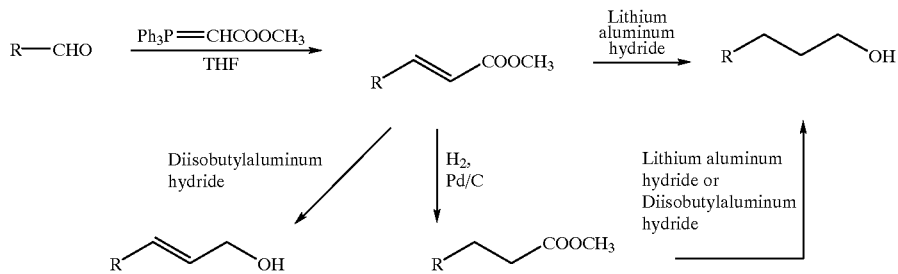

TABLE 1

In Vitro Test Results - Formulas I to V

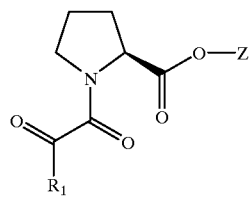

| No. | Z | R$_1$ | K$_i$ |
|---|---|---|---|
| 1 | 1,1-dimethylpropyl | 3-phenylpropyl | 42 |
| 2 | " | 3-phenyl-prop-2-(E)-enyl | 125 |
| 3 | " | 3-(3,4,5-trimethoxy-phenyl)propyl | 200 |
| 4 | " | 3-(3,4,5-trimethoxy-phenyl)-prop-2-(E)-enyl | 65 |
| 5 | " | 3-(4,5-methylenedioxy)-phenylpropyl | 170 |
| 6 | " | 3-(4,5-methylenedioxy)phenylprop-2-(E)-enyl | 160 |
| 7 | " | 3-cyclohexylpropyl | 200 |
| 8 | " | 3-cyclohexylprop-2-(E)-enyl | 600 |
| 9 | " | (1R)-1,3-diphenyl-1- propyl | 52 |
| 10 | 2-furanyl | 3-phenylpropyl | 4000 |
| 11 | 2-thienyl | " | 92 |
| 12 | 2-thiazolyl | " | 100 |
| 13 | phenyl | " | 1970 |
| 14 | 1,1-dimethylpropyl | 3-(2,5-dimethoxy)phenylpropyl | 250 |
| 15 | " | 3-(2,5-dimethoxy)phenylprop-2-(E)-enyl | 450 |
| 16 | " | 2-(3,4,5-trimethoxyphenyl)ethyl | 120 |
| 17 | " | 3-(3-pyridyl)propyl | 5 |
| 18 | " | 3-(2-pyridyl)propyl | 195 |
| 19 | " | 3-(4-pyridyl)propyl | 23 |
| 20 | cyclohexyl | 3-phenylpropyl | 82 |
| 21 | tert-butyl | " | 95 |
| 22 | cyclohexylethyl | " | 1025 |
| 23 | cyclohexylethyl | 3-(3-pyridyl)propyl | 1400 |
| 24 | tert-butyl | 3-(3-pyridyl)propyl | 3 |
| 25 | 1,1-dimethylpropyl | 3,3-diphenylpropyl | 5 |
| 26 | cyclohexyl | 3-(3-pyridyl)propyl | 9 |
| 27 | 2-thienyl | 3-(3-pyridyl)propyl | 1000 |
| 28 | tert-butyl | 3,3-diphenylpropyl | 5 |
| 29 | cyclohexyl | " | 20 |
| 30 | 2-thienyl | " | 150 |

Route of Administration

To effectively treat alopecia or promote hair growth, the compounds used in the inventive methods and pharmaceutical compositions must readily affect the targeted areas. For these purposes, the compounds are preferably administered topically to the skin.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Other routes of administration known in the pharmaceutical art are also contemplated by this invention.

Dosage

Dosage levels on the order of about 0.1 mg to about 10,000 mg of the active ingredient compound are useful in the treatment of the above conditions, with preferred levels of about 0.1 mg to about 1,000 mg. The specific dose level for any particular patient will vary depending upon a variety of factors, including the activity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

The compounds can be administered with other hair revitalizing agents. Specific dose levels for the other hair revitalizing agents will depend upon the factors previously stated and the effectiveness of the drug combination.

EXAMPLES

The following examples are illustrative of the present invention and are not intended to be limitations thereon. Unless otherwise indicated, all percentages are based upon 100% by weight of the final composition.

Example 1

Synthesis of 3-phenyl-1-propyl (2S)-1-(3,3-dimethyl-1,2-dioxopentyl)-2-pyrrolidinecarboxylate (1)

Methyl (2S)-1-(1,2-dioxo-2-methoxyethyl)-2-pyrrolidinecarboxylate

A solution of L-proline methyl ester hydrochloride (3.08 g; 18.60 mmol) in dry methylene chloride was cooled to 0° C. and treated with triethylamine (3.92 g; 38.74 mmol; 2.1 eq). After stirring the formed slurry under a nitrogen atmosphere for 15 min, a solution of methyl oxalyl chloride (3.20 g; 26.12 mmol) in methylene chloride (45 mL) was added dropwise. The resulting mixture was stirred at 0° C. for 1.5 hour. After filtering to remove solids, the organic phase was washed with water, dried over MgSO$_4$ and concentrated. The crude residue was purified on a silica gel column, eluting with 50% ethyl acetate in hexane, to obtain 3.52 g (88%) of the product as a reddish oil. Mixture of cis-trans amide rotamers; data for trans rotamer given. $^1$H NMR (CDCl$_3$): d 1.93 (dm, 2H) ; 2.17 (m, 2H) ; 3.62 (m, 2H) ; 3.71 (s, 3H);
3.79, 3.84 (s, 3H total); 4.86 (dd, 1H, J=8.4, 3.3).

Methyl (2S)-1-(1,2-dioxo-3,3-dimethylpentyl)-2-pyrrolidinecarboxylate

A solution of methyl (2S)-1-(1,2-dioxo-2-methoxyethyl)-2-pyrrolidinecarboxylate (2.35 g; 10.90 mmol) in 30 mL of tetrahydrofuran (THF) was cooled to −78° C. and treated with 14.2 mL of a 1.0 M solution of 1,1-dimethylpropylmagnesium chloride in THF. After stirring the resulting homogeneous mixture at −78° C. for three hours, the mixture was poured into saturated ammonium chloride (100 mL) and extracted into ethyl acetate. The organic phase was washed with water, dried, and concentrated, and the crude material obtained upon removal of the solvent was purified on a silica gel column, eluting with 25% ethyl acetate in hexane, to obtain 2.10 g (75%) of the oxamate as a colorless oil. $^1$H NMR (CDCl$_3$) d 0.88 (t, 3H); 1.22, 1.26 (s, 3H each); 1.75 (dm, 2H); 1.87–2.10 (m, 3H); 2.23 (m, 1H); 3.54 (m, 2H); 3.76 (s, 3H); 4.52 (dm, 1H, J=8.4, 3.4).

Synthesis of (2S)-1-(1,2-dioxo-3,3-dimethylpentyl)-2-pyrrolidinecarboxylic acid

A mixture of methyl (2S)-1-(1,2-dioxo-3,3-dimethylpentyl)-2-pyrrolidinecarboxylate (2.10 g; 8.23 mmol), 1 N LiOH (15 mL), and methanol (50 mL) was stirred at 0° C. for 30 minutes and at room temperature overnight. The mixture was acidified to pH 1 with 1 N HCl, diluted with water, and extracted into 100 mL of methylene chloride. The organic extract was washed with brine and concentrated to deliver 1.73 g (87%) of snow-white solid which did not require further purification. $^1$H NMR (CDCl$_3$): d 0.87 (t, 3H); 1.22, 1.25 (s, 3H each); 1.77 (dm, 2H); 2.02 (m, 2H); 2.17 (m, 1H); 2.25 (m, 1H); 3.53 (dd, 2H, J=10.4, 7.3); 4.55 (dd, 1H, J=8.6, 4.1).

3-Phenyl-1-propyl (2S)-1-(3,3-dimethyl-1,2-dioxopentyl)-2-pyrrolidinecarboxylate (1)

A mixture of (2S)-1-(1,2-dioxo-3,3-dimethylpentyl)-2-pyrrolidine-carboxylic acid (600 mg; 2.49 mmol), 3-phenyl-1-propanol (508 mg; 3.73 mmol), dicyclohexylcarbodiimide (822 mg; 3.98 mmol), camphorsulfonic acid (190 mg; 0.8 mmol) and 4-dimethylaminopyridine (100 mg; 0.8 mmol) in methylene chloride (20 mL) was stirred overnight under a nitrogen atmosphere. The reaction mixture was filtered through Celite to remove solids and concentrated in vacuo, and the crude material was purified on a flash column (25% ethyl acetate in hexane) to obtain 720 mg (80%) of Example 1 as a colorless oil. $^1$H NMR (CDCl$_3$): d 0.84 (t, 3H); 1.19 (s, 3H); 1.23 (s, 3H); 1.70 (dm, 2H); 1.98 (m, 5H); 2.22 (m, 1H) ; 2.64 (m, 2H) ; 3.47 (m, 2H) ; 4.14 (m, 2H); 4.51 (d, 1H); 7.16 (m, 3H); 7.26 (m, 2H).

Example 2

The method of Example 1 was utilized to prepare the following illustrative compounds.

Compound 2: 3-phenyl-1-prop-2-(E)-enyl (2S)-1-(3,3-dimethyl-1,2-dioxopentyl)-2-pyrrolidinecarboxylate, 80%. $^1$H NMR (360 Mhz, CDCl$_3$): d 0.86 (t, 3H); 1.21 (s, 3H); 1.25 (s, 3H); 1.54–2.10 (m, 5H); 2.10–2.37 (m, 1H); 3.52–3.55 (m, 2H); 4.56 (dd, 1H, J=3.8, 8.9); 4.78–4.83 (m, 2H); 6.27 (m, 1H); 6.67 (dd, 1H, J=15.9); 7.13–7.50 (m, 5H).

Compound 3: 3-(3,4,5-trimethoxyphenyl)-1-propyl (2S) -1-(3,3-dimethyl-1,2-dioxopentyl)-2-pyrrolidinecarboxylate, 61%. $^1$H NMR (CDCl$_3$): d 0.84 (t, 3H); 1.15 (s, 3H); 1.24 (s, 3H); 1.71 (dm, 2H); 1.98 (m, SH); 2.24 (m, 1H); 2.63 (m, 2H); 3.51 (t, 2H); 3.79 (s, 3H) ; 3.83 (s, 3H) ; 4.14 (m, 2H) ; 4.52 (m, 1H) 6.36 (s, 2H).

Compound 4: 3-(3,4,5-trimethoxyphenyl)-1-prop-2-(E)-enyl (2S)-1-(3,3-dimethyl-1,2-dioxopentyl)-2-pyrrolidine carboxylate, 66%. $^1$H NMR (CDCl$_3$): d 0.85 (t, 3H); 1.22 (s, 3H); 1.25 (s, 3H); 1.50–2.11 (m, 5H); 2.11–2.40 (m, 1H); 3.55 (m, 2H); 3.85 (s, 3H); 3.88 (s, 6H); 4.56 (dd, 1H); 4.81 (m, 2H); 6.22 (m, 1H); 6.58 (d, 1H, J=16); 6.63 (s, 2H).

Compound 5: 3-(4,5-methylenedioxyphenyl)-1-propyl (2S)-1-(3,3-dimethyl-1,2-dioxopentyl)-2-pyrrolidinecarboxylate, 82%. $^1$H NMR (360 MHz, CDCl$_3$) : d 0.86 (t, 3H); 1.22 (s, 3H); 1.25 (s, 3H); 1.60–2.10 (m, 5H); 3.36–3.79 (m, 2H); 4.53 (dd, 1H, J=3.8, 8.6); 4.61–4.89 (m, 2H); 5.96 (s, 2H); 6.10 (m, 1H); 6.57 (dd, 1H, J=6.2, 15.8); 6.75 (d, 1H, J=8.0); 6.83 (dd, 1H, J=1.3, 8.0); 6.93 (s, 1H).

Compound 6: 3-(4,5-methylenedioxyphenyl)-1-prop-2-(E)-enyl (2S)-1-(3,3-dimethyl-1,2-dioxopentyl)-2-pyrrolidinecarboxylate, 82%. $^1$H NMR (360 MHz, CDCl$_3$): d 0.86 (t, 3H); 1.22 (s, 3H); 1.25 (s, 3H); 1.60–2.10 (m, 5H); 2.10–2.39 (m, 1H); 3.36–3.79 (m, 2H); 4.53 (dd, 1H, J 3.8, 8.6); 4.61–4.89 (m, 2H); 5.96 (s, 2H); 6.10 (m, 1H); 6.57 (dd, 1H, J=6.2, 15.8); 6.75 (d, 1H, J=8.0); 6.83 (dd, 1H, J=1.3, 8.0); 6.93 (s, 1H).

Compound 8: 3-cyclohexyl-1-prop-2-(E)-enyl (2S)-1-(3,3-dimethyl-1,2-dioxopentyl)-2-pyrrolidinecarboxylate, 92%. $^1$H NMR (360 MHz, CDCl$_3$): d 0.86 (t, 3H); 1.13–1.40 (m+2 singlets, 9H total); 1.50–1.87 (m, 8H); 1.87–2.44 (m, 6H); 3.34–3.82 (m, 2H); 4.40–4.76 (m, 3H); 5.35–5.60 (m, 1H); 5.60–5.82 (dd, 1H, J=6.5, 16).

Compound 9: (1R)-1,3-Diphenyl-1-propyl (2S)-1-(3,3-dimethyl-1,2-dioxopentyl)-2-pyrrolidinecarboxylate, 90%. $^1$H NMR (360 MHz, CDCl$_3$) : d 0.85 (t, 3H); 1.20 (s, 3H); 1.23 (s, 3H); 1.49–2.39 (m, 7H); 2.46–2.86 (m, 2H); 3.25–3.80 (m, 2H); 4.42–4.82 (m, 1H); 5.82 (td, 1H, J=1.8, 6.7); 7.05–7.21 (m, 3H); 7.21–7.46 (m, 7H).

Compound 10: 3-phenyl-1-propyl (2S)-1-(1,2-dioxo-2-[2-furanyl])ethyl-2-pyrrolidinecarboxylate, 99%. $^1$H NMR (300 MHz, CDCl$_3$): d 1.66–2.41 (m, 6H); 2.72 (t, 2H, J=7.5); 3.75 (m, 2H); 4.21 (m, 2H); 4.61 (m, 1H); 6.58 (m, 1H); 7.16–7.29 (m, 5H); 7.73 (m, 2H).

Compound 11: 3-phenyl-1-propyl (2S)-1-(1,2-dioxo-2-[2-thienyl])ethyl-2-pyrrolidinecarboxylate, 81%. $^1$H NMR (300 MHz, CDCl$_3$): d 1.88–2.41 (m, 6H); 2.72 (dm, 2H); 3.72 (m, 2H); 4.05 (m, 1H); 4.22 (m, 1H); 4.64 (m, 1H); 7.13–7.29 (m, 6H); 7.75 (dm, 1H); 8.05 (m, 1H).

Compound 13: 3-phenyl-1-propyl (2S)-1-(1,2-dioxo-2-phenyl)ethyl-2-pyrrolidinecarboxylate, 99%. $^1$H NMR (300 MHz, CDCl$_3$) : d 1.97–2.32 (m, 6H) ; 2.74 (t, 2H, J=7.5); 3.57 (m, 2H); 4.24 (m, 2H); 4.67 (m, 1H); 6.95–7.28 (m, 5H); 7.51–7.64 (m, 3H); 8.03–8.09 (m, 2H).

Compound 14: 3-(2,5-dimethoxyphenyl)-1-propyl (2S)-1-(3,3-dimethyl-1,2-dioxopentyl)-2-pyrrolidinecarboxylate, 99%. $^1$H NMR (300 MHz, CDCl$_3$) : d 0.87 (t, 3H); 1.22 (s, 3H); 1.26 (s, 3H); 1.69 (m, 2H); 1.96 (m, 5H) ; 2.24 (m, 1H) ; 2.68 (m, 2H) ; 3.55 (m, 2H); 3.75 (s, 3H); 3.77 (s, 3H); 4.17 (m, 2H); 4.53 (d, 1H) ; 6.72 (m, 3H).

Compound 15: 3-(2,5-dimethoxyphenyl)-1-prop-2-(E)-enyl (2S)-1-(3,3-dimethyl-1,2-dioxopentyl)-2-pyrrolidinecarboxylate, 99%. $^1$H NMR (300 MHz, CDCl$_3$): d 0.87 (t, 3H) ; 1.22 (s, 3H) ; 1.26 (s, 3H) 1.67 (m, 2H); 1.78 (m, 1H); 2.07 (m, 2H); 2.26 (m, 1H); 3.52 (m, 2H); 3.78 (s, 3H); 3.80 (s, 3H); 4.54 (m, 1H); 4.81 (m, 2H); 6.29 (dt, 1H, J=15.9); 6.98 (s, 1H).

Compound 16: 2-(3,4,5-trimethoxyphenyl)-1-ethyl (2S)-1-(3,3-dimethyl-1,2-dioxopentyl)-2-pyrrolidinecarboxylate, 97%. $^1$H NMR (300 MHz, CDCl$_3$) : d 0.84 (t, 3H); 1.15 (s, 3H) ; 1.24 (s, 3H); 1.71 (dm, 2H) ; 1.98 (m, 5H); 2.24 (m, 1H); 2.63 (m, 2H); 3.51 (t, 2H); 3.79 (s, 3H); 3.83 (s, 3H); 4.14 (m, 2H); 4.52 (m, 1H) ; 6.36 (s, 2H).

Compound 17: 3-(3-Pyridyl)-1-propyl (2S)-1-(3,3-dimethyl-1,2-dioxopentyl)-2-pyrrolidinecarboxylate, 80%. $^1$H NMR (CDCl$_3$, 300 MHz) : d 0.85 (t, 3H) ; 1.23, 1.26 (s, 3H each); 1.63–1.89 (m, 2H); 1.90–2.30 (m, 4H); 2.30–2.50 (m, 1H); 2.72 (t, 2H); 3.53 (m, 2H); 4.19 (m, 2H); 4.53 (m, 1H); 7.22 (m, 1H); 7.53 (dd, 1H); 8.45.

Compound 18: 3-(2-Pyridyl)-1-propyl (2S)-1-(3,3-dimethyl-1,2-dioxopentyl)-2-pyrrolidinecarboxylate, 88%. $^1$H NMR (CDCl$_3$, 300 MHz): d 0.84 (t, 3H); 1.22, 1.27 (s, 3H each); 1.68–2.32 (m, 8H); 2.88 (t, 2H, J=7.5); 3.52 (m, 2H); 4.20 (m, 2H); 4.51 (m, 1H); 7.09–7.19 (m, 2H); 7.59 (m, 1H); 8.53 (d, 1H, J 4.9).

Compound 19: 3-(4-Pyridyl)-1-propyl (2S)-1-(3,3-dimethyl-1,2-dioxopentyl)-2-pyrrolidinecarboxylate, 91%. $^1$H NMR (CDCl$_3$, 300 MHz): d 6.92–6.80 (m, 4H); 6.28 (m, 1H); 5.25 (d, 1H, J 5.7); 4.12 (m, 1H); 4.08 (s, 3H); 3.79 (s, 3H); 3.30 (m, 2H); 2.33 (m, 1H); 1.85–1.22 (m, 7H); 1.25 (s, 3H); 1.23 (s, 3H); 0.89 (t, 3H, J=7.5).

Compound 20: 3-phenyl-1-propyl (2S)-1-(2-cyclohexyl-1,2-dioxoethyl)-2-pyrrolidinecarboxylate, 91%. $^1$H NMR (CDCl$_3$, 300 MHz): d 1.09–1.33 (m, 5H); 1.62–2.33 (m, 12H); 2.69 (t, 2H, J=7.5); 3.15 (dm, 1H); 3.68 (m, 12H); 4.16 (m, 2H); 4.53, 4.84 (d, 1H total); 7.19 (m, 3H); 7.29 (m, 2H).

Compound 21: 3-phenyl-1-propyl (2S)-1-(2-tert-butyl-1,2-dioxoethyl)-2-pyrrolidinecarboxylate, 92%. $^1$H NMR (CDCl$_3$, 300 MHz): d 1.29 (s, 9H); 1.94–2.03 (m, 5H); 2.21 (m, 1H); 2.69 (m, 2H); 3.50–3.52 (m, 2H); 4.16 (m, 2H); 4.53 (m, 1H); 7.19 (m, 3H); 7.30 (m, 2H).

Compound 22: 3-phenyl-1-propyl (2S)-1-(2-cyclohexyl-ethyl-1,2-dioxoethyl)-2-pyrrolidinecarboxylate, 97%. $^1$H NMR (CDCl$_3$, 300 MHz): d 0.88 (in, 2H); 1.16 (m, 4H); 1.43–1.51 (m, 2H); 1.67 (m, 5H); 1.94–2.01 (m, 6H); 2.66–2.87 (m, 4H); 3.62–3.77 (m, 2H); 4.15 (m, 2H); 4.86 (m, 1H); 7.17–7.32 (m, 5H).

Compound 23: 3-(3-pyridyl)-1-propyl (2S)-1-(2-cyclohexylethyl-1,2-dioxoethyl)-2-pyrrolidinecarboxylate, 70%. $^1$H NMR (CDCl$_3$, 300 MHz): d 0.87 (m, 2H); 1.16 (m, 4H); 1.49 (m, 2H); 1.68 (m, 4H); 1.95–2.32 (m, 7H); 2.71 (m, 2H); 2.85 (m, 2H); 3.63–3.78 (m, 2H); 4.19 (m, 2H); 5.30 (m, 1H); 7.23 (m, 1H); 7.53 (m, 1H); 8.46 (m, 2H).

Compound 24: 3-(3-pyridyl)-1-propyl (2S)-1-(2-tert-butyl-1,2-dioxoethyl)-2-pyrrolidinecarboxylate, 83%. $^1$H NMR (CDCl$_3$, 300 MHz): d 1.29 (s, 9H); 1.95–2.04 (m, 5H); 2.31 (m, 1H); 2.72 (t, 2H, J=7.5); 3.52 (m, 2H); 4.18 (m, 2H); 4.52 (m, 1H); 7.19–7.25 (m, 1H); 7.53 (m, 1H); 8.46 (m, 2H).

Compound 25: 3,3-diphenyl-1-propyl (2S)-1-(3,3-dimethyl-1,2-dioxopentyl)-2-pyrrolidinecarboxylate, 99%. $^1$H NMR (CDCl$_3$, 300 MHz): d 0.85 (t, 3H); 1.21, 1.26 (s, 3H each); 1.68–2.04 (m, 5H); 2.31 (m, 1H); 2.40 (m, 2H); 3.51 (m, 2H); 4.08 (m, 3H); 4.52 (m, 1H); 7.18–7.31 (m, 10H).

Compound 26: 3-(3-pyridyl)-1-propyl (2S)-1-(2-cyclohexyl-1,2-dioxoethyl)-2-pyrrolidinecarboxylate, 88%. $^1$H NMR (CDCl$_3$, 300 MHz): d 1.24–1.28 (m, 5H); 1.88–2.35 (m, 11H); 2.72 (t, 2H, J=7.5); 3.00–3.33 (dm, 1H); 3.69 (m, 2H); 4.19 (m, 2H); 4.55 (m, 1H); 7.20–7.24 (m, 1H); 7.53 (m, 1H); 8.47 (m, 2H).

Compound 27: 3-(3-Pyridyl)-1-propyl (2S)-N-([2-thienyl] glyoxyl)pyrrolidinecarboxylate, 49%. $^1$H NMR (CDCl$_3$, 300 MHz): d 1.81–2.39 (m, 6H); 2.72 (dm, 2H); 3.73 (m, 2H); 4.21 (m, 2H); 4.95 (m, 1H); 7.19 (m, 2H); 7.61 (m, 1H); 7.80 (d, 1H); 8.04 (d, 1H); 8.46 (m, 2H).

Compound 28: 3,3-Diphenyl-1-propyl (2S)-1-(3,3-dimethyl-1,2-dioxobutyl)-2-pyrrolidinecarboxylate, 99%. $^1$H NMR (CDCl$_3$, 300 MHz): d 1.27 (s, 9H); 1.96 (m, 2H); 2.44 (m, 4H); 3.49 (m, 1H); 3.64 (m, 1H); 4.08 (m, 4H); 4.53 (dd, 1H); 7.24 (m, 10H).

Compound 29: 3,3-Diphenyl-1-propyl (2S)-1-cyclohexyl glyoxyl-2-pyrrolidinecarboxylate, 91%. $^1$H NMR (CDCl$_3$, 300 MHz): d 1.32 (m, 6H) ; 1.54–2.41 (m, 10H) ; 3.20 (dm, 1H); 3.69 (m, 2H); 4.12 (m, 4H); 4.52 (d, 1H); 7.28 (m, 10H).

Compound 30: 3,3-Diphenyl-1-propyl (2S)-1-(2-thienyl) glyoxyl-2-pyrrolidinecarboxylate, 75%. $^1$H NMR (CDCl$_3$, 300 MHz): d 2.04 (m, 3H) ; 2.26 (m, 2H) ; 2.48 (m, 1H) 3.70 (m, 2H); 3.82–4.18 (m, 3H total); 4.64 (m, 1H); 7.25 (m, 11H); 7.76 (dd, 1H); 8.03 (m, 1H).

Example 3

General procedure for the synthesis of acrylic esters, exemplified for methyl (3,3,5-trimethoxy)-trans-cinnamate.

A solution of 3,4,5-trimethoxybenzaldehyde (5.0 g; 25.48 mmol) and methyl (triphenylphosphoranylidene)acetate (10.0 g; 29.91 mmol) in tetrahydrofuran (250 mL) was refluxed overnight. After cooling, the reaction mixture was diluted with 200 mL of ethyl acetate and washed with 2×200 mL of water, dried, and concentrated in vacuo. The crude residue was chromatographed on a silica gel column, eluting with 25% ethyl acetate in hexane, to obtain 5.63 g (88%) of the cinnamate as a white crystalline solid. $^1$H NMR (300 Mhz; CDCl$_3$) d 3.78 (s, 3H); 3.85 (s, 6H); 6.32 (d, 1H, J16); 6.72 (s, 2H); 7.59 (d, 1H, J=16).

Example 4

General procedure for the synthesis of saturated alcohols from acrylic esters, exemplified for (3,4,5-trimethoxy) phenylpropanol.

A solution of methyl (3,3,5-trimethoxy)-trans-cinnamate (1.81 g; 7.17 mmol) in tetrahydrofuran (30 mL) was added in a dropwise manner to a solution of lithium aluminum hydride (14 mmol) in THF (35 mL), with stirring and under an argon atmosphere. After the addition was complete, the mixture was heated to 75° C. for 4 hours. After cooling, it was quenched by the careful addition of 15 mL of 2 N NaOH followed by 50 mL of water. The resulting mixture was filtered through Celite to remove solids, and the filter cake was washed with ethyl acetate. The combined organic fractions were washed with water, dried, concentrated in vacuo, and purified on a silica gel column, eluting with ethyl acetate to obtain 0.86 g (53%) of the alcohol as a clear oil. $^1$H NMR (300 Mhz; CDCl$_3$): d 1.23 (br, 1H); 1.87 (m, 2H); 2.61 (t, 2H, J=7.1); 3.66 (t, 2H); 3.80 (s, 3H); 3.83 (s, 6H); 6.40 (s, 2H).

Example 5

General procedure for the synthesis of transallylic alcohols from acrylic esters, exemplified for (3,4,5-trimethoxy) phenylprop-2-(E)-enol.

A solution of methyl (3,3,5-trimethoxy)-transcinnamate (1.35 g; 5.35 mmol) in toluene (25 mL) was cooled to −10° C. and treated with a solution of diisobutylaluminum hydride in toluene (11.25 mL of a 1.0 M solution; 11.25 mmol). The reaction mixture was stirred for 3 hours at 0° C. and then quenched with 3 mL of methanol followed by 1 N HCl until the pH was 1. The reaction mixture was extracted into ethyl acetate and the organic phase was washed with water, dried and concentrated. Purification on a silica gel column eluting with 25% ethyl acetate in hexane furnished 0.96 g (80%) of a thick oil. $^1$H NMR (360 Mhz; CDCl$_3$) d 3.85 (s, 3H); 3.87 (s, 6H); 4.32 (d, 2H, J 5.6); 6.29 (dt, 1H, J=15.8, 5.7), 6.54 (d, 1H, J=15.8); 6.61 (s, 2H).

Example 6

In Vivo Hair Generation Tests With C57 Black 6 Mice

Figure 2:
FIG. 2 is a photograph of mice treated with a vehicle after six weeks.
Figure 3:
FIG. 3 is a photograph of mice treated with 10 $\mu$M of GPI 1046, one of the non-immunosuppressive pyrrolidine derivative neuroimmunophilin FKBP ligands of this application, after six weeks.
Figure 4:
FIG. 4 is a photograph of mice treated with 30 $\mu$M of GPI 1046 after six weeks.

Experiment A: C57 black 6 mice were used to demonstrate the hair revitalizing properties of a low molecular weight, small molecule non-immunosuppressive neuroimmunophilin FKBP ligand, GPI 1046, a pyrrolidine derivative. Referring now to FIGS. 1 and 2 of the drawings, C57 black 6 mice, approximately 7 weeks old, had an area of about 2 inches by 2 inches on their hindquarters shaved to remove all existing hair. Care was taken not to nick or cause abrasion to the underlaying dermal layers. The animals were in anagen growth phase, as indicated by the pinkish color of the skin. Referring now to FIGS. 2, 3 and 4, four animals per group were treated by topical administration with 20% propylene glycol vehicle (FIG. 2), 10 μM GPI 1046 (FIG. 3) or 30 μM GPI 1046 (FIG. 4) dissolved in the vehicle. The animals were treated with vehicle or GPI 1046 every 48 hours (3 applications total over the course of 5 days) and the hair growth was allowed to proceed for 6 weeks. Hair growth was quantitated by the percent of shaved area covered by new hair growth during this time period.

FIG. 2 shows that animals treated with vehicle exhibited only a small amount of hair growth in patches or tufts, with less than 3% of the shaved area covered with new growth. In contrast, FIG. 3 shows that animals treated with 10 μM GPI 1046 exhibited dramatic hair growth, covering greater than 90% of the shaved area in all animals. Further, FIG. 4 shows that mice treated with 30 μM GPI 1046 exhibited essentially complete hair regrowth and their shaved areas were indistinguishable from unshaven C57 black 6 mice.

Experiment B: C57 Black 6 mice were used to demonstrate the hair revitalizing properties of various low molecular weight, small molecule, non-immunosuppressive neuroimmunophilin FKBP ligands, including GPI 1046. C57 Black 6 mice, 55 to 75 days old, had an area of about 2 inches by 2 inches on their hindquarters shaved to remove all existing hair. Care was taken not to nick or cause abrasion to the underlying dermal layers. The animals were in anagen growth phase when shaved. Five animals per group were treated by topical administration with a vehicle, FK506, or one of the low molecular weight, small molecule, non-immunosuppressive neuroimmunophilin FKBP ligands (GPI 1605, 1046, 1312, 1572, 1389, 1511, and 1234) at a concentration of one micromole per milliliter to the shaved area. The animals were treated three times per week, and hair growth was evaluated 14 days after initiation of treatment. Hair growth was quantitated by the percent of shaved area covered by new hair growth, as scored by a blinded observer, on a scale of 0 (no growth) to five (complete hair regrowth in shaved area).

FIG. 5 shows that after 14 days, the animals treated with vehicle exhibited the beginning of growth in small tufts. In contrast, animals treated with one of the low molecular weight, small molecule, non-immunosuppressive neuroimmunophilin FKBP ligands, including GPI 1046, exhibited dramatic hair growth.

Example 7

A lotion comprising the following composition may be prepared.

|  | (%) |
|---|---|
| 95% Ethanol | 80.0 |
| a pyrrolidine derivative as defined above | 10.0 |
| α-Tocopherol acetate | 0.01 |
| Ethylene oxide (40 mole) adducts of hardened castor oil | 0.5 |
| purified water | 9.0 |
| perfume and dye | q.s. |

Into 95% ethanol are added a pyrrolidine derivative, α-tocopherol acetate, ethylene oxide (40 mole) adducts of hardened castor oil, perfume and a dye. The resulting mixture is stirred and dissolved, and purified water is added to the mixture to obtain a transparent liquid lotion.

5 ml of the lotion may be applied once or twice per day to a site having marked baldness or alopecia.

Example 8

A lotion comprising the following composition shown may be prepared.

|  | (%) |
|---|---|
| 95% Ethanol | 80.0 |
| a pyrrolidine derivative as defined above | 0.005 |
| Hinokitol | 0.01 |
| Ethylene oxide (40 mole) adducts of hardened castor oil | 0.5 |
| Purified water | 19.0 |
| Perfume and dye | q.s |

Into 95% ethanol are added a pyrrolidine derivative, hinokitol, ethylene oxide (40 mole) adducts of hardened castor oil, perfume, and a dye. The resulting mixture is stirred, and purified water is added to the mixture to obtain a transparent liquid lotion.

The lotion may be applied by spraying once to 4 times per day to a site having marked baldness or alopecia.

Example 9

An emulsion may be prepared from A phase and B phase having the following compositions.

|  | (%) |
|---|---|
| (A phase) |  |
| Whale wax | 0.5 |
| Cetanol | 2.0 |
| Petrolatum | 5.0 |
| Squalane | 10.0 |
| Polyoxyethylene (10 mole) monostearate | 2.0 |
| Sorbitan monooleate | 1.0 |
| a pyrrolidine derivative as defined above | 0.01 |
| (B phase) |  |
| Glycerine | 10.0 |
| Purified water | 69.0 |
| Perfume, dye, and preservative | q.s. |

The A phase and the B phase are respectively heated and melted and maintained at 80° C. Both phases are then mixed and cooled under stirring to normal temperature to obtain an emulsion.

The emulsion may be applied by spraying once to four times per day to a site having marked baldness or alopecia.

Example 10

A cream may be prepared from A phase and B phase having the following compositions.

|  | (%) |
|---|---|
| (A Phase) |  |
| Fluid paraffin | 5.0 |
| Cetostearyl alcohol | 5.5 |
| Petrolatum | 5.5 |
| Glycerine monostearate | 33.0 |
| Polyoxyethylene (20 mole) 2-octyldodecyl ether | 3.0 |
| Propylparaben | 0.3 |
| (B Phase) |  |
| a pyrrolidine derivative as defined above | 0.8 |
| Glycerine | 7.0 |
| Dipropylene glycol | 20.0 |
| Polyethylene glycol 4000 | 5.0 |

-continued

| | (%) |
|---|---|
| Sodium Hexametaphosphate | 0.005 |
| Purified water | 44.895 |

The A phase is heated and melted, and maintained at 70° C. The B phase is added into the A phase and the mixture is stirred to obtain an emulsion. The emulsion is then cooled to obtain a cream.

The cream may be applied once to 4 times per day to a site having marked baldness or alopecia.

Example 11

A liquid comprising the following composition may be prepared.

| | (%) |
|---|---|
| Polyoxyethylene butyl ether | 20.0 |
| Ethanol | 50.0 |
| a pyrrolidine derivative as defined above | 0.001 |
| Propylene glycol | 5.0 |
| Polyoxyethylene hardened castor oil derivative (ethylene oxide 80 mole adducts) | 0.4 |
| Perfume | q.s. |
| Purified water | q.s. |

Into ethanol are added polyoxypropylene butyl ether, propylene glycol, polyoxyethylene hardened castor oil, a pyrrolidine derivative, and perfume. The resulting mixture is stirred, and purified water is added to the mixture to obtain a liquid.

The liquid may be applied once to 4 times per day to a site having marked baldness or alopecia.

Example 12

A shampoo comprising the following composition may be prepared.

| | (%) |
|---|---|
| Sodium laurylsulfate | 5.0 |
| Triethanolamine laurylsulfate | 5.0 |
| Betaine lauryldimethylaminoacetate | 6.0 |
| Ethylene glycol distearate | 2.0 |
| Polyethylene glycol | 5.0 |
| a pyrrolidine derivative as defined above | 5.0 |
| Ethanol | 2.0 |
| Perfume | 0.3 |
| Purified water | 69.7 |

Into 69.7 of purified water are added 5.0 g of sodium laurylsulfate, 5.0 g of triethanolamine laurylsulfate, 6.0 g of betaine lauryldimethylaminoacetate. Then a mixture obtained by adding 5.0 g of a pyrrolidine derivative, 5.0 g of polyethylene glycol, and 2.0 g of ethylene glycol distearate to 2.0 g of ethanol, followed by stirring, and 0.3 g of perfume are successively added. The resulting mixture is heated and subsequently cooled to obtain a shampoo.

The shampoo may be used on the scalp once or twice per day.

Example 13

A patient is suffering from alopecia senilis. A pyrrolidine derivative as identified above, or a pharmaceutical composition comprising the same, may be administered to the patient. Increased hair growth is expected to occur following treatment.

Example 14

A patient is suffering from male pattern alopecia. A pyrrolidine derivative as identified above, or a pharmaceutical composition comprising the same may be administered to the patient. Increased hair growth is expected to occur following treatment.

Example 15

A patient is suffering from alopecia areata. A pyrrolidine derivative as identified above, or a pharmaceutical composition comprising the same, may be administered to the patient. Increased hair growth is expected to occur following treatment.

Example 16

A patient is suffering from hair loss caused by skin lesions. A pyrrolidine derivative as identified above, or a pharmaceutical composition comprising the same, may be administered to the patient. Increased hair growth is expected to occur following treatment.

Example 17

A patient is suffering from hair loss caused by tumors. A pyrrolidine derivative as identified above, or a pharmaceutical composition comprising the same, may be administered to the patient. Increased hair growth is expected to occur following treatment.

Example 18

A patient is suffering from hair loss caused by a systematic disorder, such as a nutritional disorder or an internal secretion disorder. A pyrrolidine derivative as identified above, or a pharmaceutical composition comprising the same, may be administered to the patient. Increased hair growth is expected to occur following treatment.

Example 19

A patient is suffering from hair loss caused by chemotherapy. A pyrrolidine derivative as identified above, or a pharmaceutical composition comprising the same, may be administered to the patient. Increased hair growth is expected to occur following treatment.

Example 20

A patient is suffering from hair loss caused by adiation. A pyrrolidine derivative as identified above, or a pharmaceutical composition comprising the same may, be administered to the patient. Increased hair growth is expected to occur following treatment.

The invention being thus described, it will be obvious that the same may be varied in many ways. Such variations are not to be regarded as a departure from the spirit and scope of the invention and all such modifications are intended to be included within the scope of the following claims.

We claim:

1. A method for treating alopecia or promoting hair growth in an animal in need thereof, which comprises administering to said animal an effective amount of a non-immunosuppressive five-membered heterocyclic compound having a single nitrogen heteroatom, which has an N-linked ketone, diketo, thioketo, or 1-(2-(3-oxo)propene) substituent, and which is additionally substituted with an ester or amide substituent attached to the heterocyclic ring, provided that said ester or amide substituent is not an N-oxide of an ester or amide, wherein said compound has an affinity for an FKBP-type immunophilin.

2. The method of claim 1, wherein the FKBP-type immunophilin is FKBP-12.

3. A method for treating alopecia or promoting hair growth in an animal in need thereof, which comprises administering to said animal an effective amount of a compound of formula I

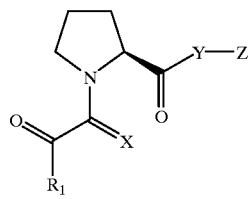

or a pharmaceutically acceptable salt, ester, or solvate thereof, wherein:
- $R_1$ is $C_1$–$C_9$ straight or branched chain alkyl, $C_2$–$C_9$ straight or branched chain alkenyl, $C_3$–$C_8$ cycloalkyl, $C_5$–$C_7$ cycloalkenyl or $Ar_1$, wherein said $R_1$ is unsubstituted or substituted with one or more substituents independently selected from the group consisting of $C_1$–$C_6$ alkyl, $C_2$–$C_6$ alkenyl, $C_3$–$C_8$ cycloalkyl, $C_5$–$C_7$ cycloalkenyl, hydroxy, and $Ar_2$;
- $Ar_1$ and $Ar_2$ are independently selected from the group consisting of 1-napthyl, 2-napthyl, 2-indolyl, 3-indolyl, 2-furyl, 3-furyl, 2-thienyl, 3-thienyl, 2-pyridyl, 3-pyridyl, 4-pyridyl and phenyl, wherein said $Ar_1$ is unsubstituted or substituted with one or more substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and amino;
- X is O, S, $CH_2$ or $H_2$;
- Y is O or $NR_2$, wherein $R_2$ is hydrogen or $C_1$–$C_6$ alkyl; and
- Z is $C_1$–$C_6$ straight or branched chain alkyl, or $C_2$–$C_6$ straight or branched chain alkenyl, wherein said Z is substituted with one or more substituent(s) independently selected from the group consisting of $Ar_1$, $C_3$–$C_8$ cycloalkyl, and $C_1$–$C_6$ straight or branched chain alkyl or $C_2$–$C_6$ straight or branched chain alkenyl substituted with $C_3$–$C_8$ cycloalkyl; or Z is fragment

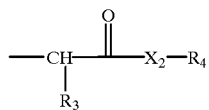

wherein:
- $R_3$ is $C_1$–$C_9$ straight or branched chain alkyl which is unsubstituted or substituted with $C_3$–$C_8$ cycloalkyl or $Ar_1$;
- $X_2$ is O or $NR_5$, wherein $R_5$ is selected from the group consisting of hydrogen, $C_1$–$C_6$ straight or branched chain alkyl, and $C_2$–$C_6$ straight or branched chain alkenyl; and
- $R_4$ is selected from the group consisting of phenyl, benzyl, $C_{1-C5}$ straight or branched chain alkyl, $C_2$–$C_5$ straight or branched chain alkenyl, $C_1$–$C_5$ straight or branched chain alkyl substituted with phenyl, and $C_2$–$C_5$ straight or branched chain alkenyl substituted with phenyl.

4. The method of claim 3, wherein Z and $R_1$ are lipophilic.

5. The method of claim 3, wherein the compound is selected from the group consisting of:
- 3-phenyl-1-propyl (2S)-1-(3,3-dimethyl-1,2-dioxopentyl)-2-pyrrolidinecarboxylate;
- 3-phenyl-1-prop-2-(E)-enyl (2S)-1-(3,3-dimethyl-1,2-dioxopentyl)-2-pyrrolidinecarboxylate;
- 3-(3,4,5-trimethoxyphenyl)-1-propyl (2S)-1-(3,3-dimethyl-1,2-dioxopentyl)-2-pyrrolidinecarboxylate;
- 3-(3,4,5-trimethoxyphenyl)-1-prop-2-(E)-enyl (2S)-1-(3,3-dimethyl-1,2-dioxopentyl)-2-pyrrolidinecarboxylate;
- 3-(4,5-dichlorophenyl)-1-propyl (2S)-1-(3,3-dimethyl-1,2-dioxopentyl)-2-pyrrolidinecarboxylate;
- 3-(4,5-dichlorophenyl)-1-prop-2-(E)-enyl (2S)-1-(3,3-dimethyl-1,2-dioxopentyl)-2-pyrrolidinecarboxylate;
- 3-(4,5-methylenedioxyphenyl)-1-propyl (2S)-1-(3,3-dimethyl-1,2-dioxopentyl)-2-pyrrolidinecarboxylate;
- 3-(4,5-methylenedioxyphenyl)-1-prop-2-(E)-enyl (2S)-1-(3,3-dimethyl-1,2-dioxopentyl)-2-pyrrolidinecarboxylate;
- 3-cyclohexyl-1-propyl (2S)-1-(3,3-dimethyl-1,2-dioxopentyl)-2-pyrrolidinecarboxylate;
- 3-cyclohexyl-1-prop-2-(E)-enyl (2S)-1-(3,3-dimethyl-1,2-dioxopentyl)-2-pyrrolidinecarboxylate;
- (1R)-1,3-diphenyl-1-propyl (2S)-1-(3,3-dimethyl-1,2-dioxopentyl)-2-pyrrolidinecarboxylate;
- (1R)-1,3-diphenyl-1-prop-2-(E)-enyl (2S)-1-(3,3-dimethyl-1,2-dioxopentyl)-2-pyrrolidinecarboxylate;
- (1R)-1-cyclohexyl-3-phenyl-1-propyl (2S)-1-(3,3-dimethyl-1,2-dioxopentyl)-2-pyrrolidinecarboxylate;
- (1R)-1-cyclohexyl-3-phenyl-1-prop-2-(E)-enyl (2S)-1-(3,3-dimethyl-1,2-dioxopentyl)-2-pyrrolidinecarboxylate;
- (1R)-1-(4,5-dichlorophenyl)-3-phenyl-1-propyl (2S)-1-(3,3-dimethyl-1,2-dioxopentyl)-2-pyrrolidinecarboxylate;
- 3-phenyl-1-propyl (2S)-1-(1,2-dioxo-2-cyclohexyl)ethyl-2-pyrrolidinecarboxylate;
- 3-phenyl-1-propyl (2S)-1-(1,2-dioxo-4-cyclohexyl)butyl-2-pyrrolidinecarboxylate;
- 3-phenyl-1-propyl (2S)-1-(1,2-dioxo-2-[2-furanyl])ethyl-2-pyrrolidinecarboxylate;
- 3-phenyl-1-propyl (2S)-1-(1,2-dioxo-2-[2-thienyl])ethyl-2-pyrrolidinecarboxylate;
- 3-phenyl-1-propyl (2S)-1-(1,2-dioxo-2-[2-thiazolyl])ethyl-2-pyrrolidinecarboxylate;
- 3-phenyl-1-propyl (2S)-1-(1,2-dioxo-2-phenyl)ethyl-2-pyrrolidinecarboxylate;
- 1,7-diphenyl-4-heptyl (2S)-1-(3,3-dimethyl-1,2-dioxopentyl)-2-pyrrolidinecarboxylate;
- 3-phenyl-1-propyl (2S)-1-(3,3-dimethyl-1,2-dioxo-4-hydroxybutyl)-2-pyrrolidinecarboxylate;
- 3-phenyl-1-propyl (2S)-1-(3,3-dimethyl-1,2-dioxopentyl)-2-pyrrolidinecarboxamide;
- 1-[1-(3,3-dimethyl-1,2-dioxopentyl)-L-proline]-L-phenylalanine ethyl ester;
- 1-[1-(3,3-dimethyl-1,2-dioxopentyl)-L-proline]-L-leucine ethyl ester;

1-[1-(3,3-dimethyl-1,2-dioxopentyl)-L-proline]-L-phenylglycine ethyl ester;

1-[1-(3,3-dimethyl-1,2-dioxopentyl)-L-proline]-L-phenylalanine phenyl ester;

1-[1-(3,3-dimethyl-1,2-dioxopentyl)-L-proline]-L-phenylalanine benzyl ester; and 1-[1-(3,3-dimethyl-1,2-dioxopentyl)-L-proline]-L-isoleucine ethyl ester;

or a pharmaceutically acceptable salt, ester, or solvate thereof.

6. A method for treating alopecia or promoting hair growth in an animal in need thereof, which comprises administering to said animal an effective amount of a compound of formula II

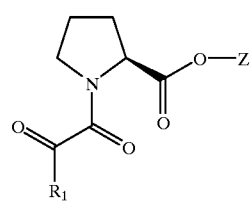

II or a pharmaceutically acceptable salt, ester, or solvate thereof, wherein:

$R_1$ is $C_1$–$C_9$ straight or branched chain alkyl, $C_2$–$C_9$ straight or branched chain alkenyl, $C_3$–$C_8$ cycloalkyl, $C_5$–$C_7$ cycloalkenyl or $Ar_1$, wherein said $R_1$ is unsubstituted or substituted with one or more substituents independently selected from the group consisting of $C_1$–$C_6$ alkyl, $C_2$–$C_6$ alkenyl, $C_3$–$C_8$ cycloalkyl, $C_5$–$C_7$ cycloalkenyl, hydroxy, and $Ar_2$;

$Ar_1$ and $Ar_2$ are independently selected from the group consisting of 1-napthyl, 2-napthyl, 2-indolyl, 3-indolyl, 2-furyl, 3-furyl, 2-thienyl, 3-thienyl, 2-pyridyl, 3-pyridyl, 4-pyridyl and phenyl, wherein said $Ar_1$ is unsubstituted or substituted with one or more substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and amino;

Z is $C_1$–$C_6$ straight or branched chain alkyl, or $C_2$–$C_6$ straight or branched chain alkenyl, wherein said Z is substituted with one or more substituent(s) independently selected from the group consisting of $Ar_1$, $C_3$–$C_8$ cycloalkyl, and $C_1$–$C_6$ straight or branched chain alkyl or $C_2$–$C_6$ straight or branched chain alkenyl substituted with $C_3$–$C_8$ cycloalkyl; or Z is fragment

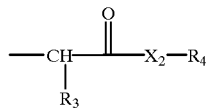

wherein:

$R_3$ is $C_1$–$C_9$ straight or branched chain alkyl which is unsubstituted or substituted with $C_3$–$C_8$ cycloalkyl or $Ar_1$;

$X_2$ is O or $NR_5$, wherein $R_5$ is selected from the group consisting of hydrogen, $C_1$–$C_6$ straight or branched chain alkyl, and $C_2$–$C_6$ straight or branched chain alkenyl; and $R_4$ is selected from the group consisting of phenyl, benzyl, $C_1$–$C_5$ straight or branched chain alkyl, $C_2$–$C_5$ straight or branched chain alkenyl, $C_1$–$C_5$ straight or branched chain alkyl substituted with phenyl, and $C_2$–$C_5$ straight or branched chain alkenyl substituted with phenyl.

7. The method of claim 6, wherein $R_1$ is selected from the group consisting of $C_1$–$C_9$ straight or branched chain alkyl, 2-cyclohexyl, 4-cyclohexyl, 2-furanyl, 2-thienyl, 2-thiazolyl, and 4-hydroxybutyl.

8. The method of claim 6, wherein Z and $R_1$ are lipophilic.

9. A method for treating alopecia or promoting hair growth in an animal in need thereof, which comprises administering to said animal an effective amount of a compound of formula III

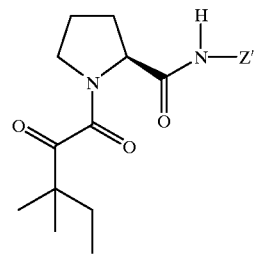

III or a pharmaceutically acceptable salt, ester, or solvate or hydrate thereof, wherein:

Z' is fragment

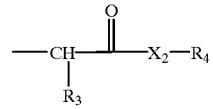

wherein:

$R_3$ is $C_1$–$C_9$ straight or branched chain alkyl or unsubstituted $Ar_1$, wherein said alkyl is unsubstituted or substituted with $C_3$–$C_8$ cycloalkyl or $Ar_1$;

$X_2$ is O or $NR_5$, wherein $R_5$ is selected from the group consisting of hydrogen, $C_1$–$C_6$ straight or branched chain alkyl, and $C_2$–$C_6$ straight or branched chain alkenyl;

$R_4$ is selected from the group consisting of phenyl, benzyl, $C_1$–$C_5$ straight or branched chain alkyl, $C_2$–$C_5$ straight or branched chain alkenyl, $C_1$–$C_5$ straight or branched chain alkyl substituted with phenyl, and $C_2$–$C_5$ straight or branched chain alkenyl substituted with phenyl; and $Ar_1$ is selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl and phenyl, wherein said $Ar_1$ is unsubstituted or substituted with one or more substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and amino.

10. The method of claim 9, wherein Z' is lipophilic.

11. A method for treating alopecia or promoting hair growth in an animal in need thereof, which comprises administering to said animal an effective amount of a compound of formula IV

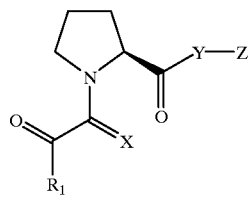

IV or a pharmaceutically acceptable salt, ester, or solvate thereof, wherein:

$R_1$ is $C_1$–$C_6$ straight or branched chain alkyl, $C_2$–$C_6$ straight or branched chain alkenyl, $C_3$–$C_6$ cycloalkyl or $Ar_1$, wherein said alkyl or alkenyl is unsubstituted or substituted with $C_3$–$C_6$ cycloalkyl or $Ar_2$;

$Ar_1$ and $Ar_2$ are independently selected from the group consisting of 2-furyl, 2-thienyl, and phenyl;

X is selected from the group consisting of oxygen and sulfur;

Y is oxygen;

Z is $C_1$–$C6$ straight or branched chain alkyl, or $C_2$–$C_6$ straight or branched chain alkenyl, wherein said Z is substituted with one or more substituent(s) independently selected from the group consisting of 2-furyl, 2-thienyl, $C_3$–$C_6$ cycloalkyl, pyridyl, and phenyl, each having one or more substituent(s) independently selected from the group consisting of hydrogen and $C_1$–$C_4$ alkoxy.

12. The method of claim 11, wherein Z and $R_1$ are lipophilic.

13. The method of claim 11, wherein the compound is selected from the group consisting of:

3-(2,5-dimethoxyphenyl)-1-propyl (2S)-1-(3,3-dimethyl-1,2-dioxopentyl)-2-pyrrolidinecarboxylate;

3-(2,5-dimethoxyphenyl)-1-prop-2-(E)-enyl (2S)-1-(3,3-dimethyl-1,2-dioxopentyl)-2-pyrrolidinecarboxylate;

2-(3,4,5-trimethoxyphenyl)-1-ethyl (2S)-1-(3,3-dimethyl-1,2-dioxopentyl)-2-pyrrolidinecarboxylate;

3-(3-pyridyl)-1-propyl (2S)-1-(3,3-dimethyl-1,2-dioxopentyl)-2-pyrrolidinecarboxylate;

3-(2-pyridyl)-1-propyl (2S)-1-(3,3-dimethyl-1,2-dioxopentyl)-2-pyrrolidinecarboxylate;

3-(4-pyridyl)-1-propyl (2S)-1-(3,3-dimethyl-1,2-dioxopentyl)-2-pyrrolidinecarboxylate;

3-phenyl-1-propyl (2S)-1-(2-tert-butyl-1,2-dioxoethyl)-2-pyrrolidinecarboxylate;

3-phenyl-1-propyl (2S)-1-(2-cyclohexylethyl-1,2-dioxoethyl)-2-pyrrolidinecarboxylate;

3-(3-pyridyl)-1-propyl (2S)-1-(2-cyclohexylethyl-1,2-dioxoethyl)-2-pyrrolidinecarboxylate;

3-(3-pyridyl)-1-propyl (2S)-1-(2-tert-butyl-1,2-dioxoethyl)-2-pyrrolidinecarboxylate;

3-(3-diphenyl)-1-propyl (2S)-1-(3,3-dimethyl-1,2-dioxopentyl)-2-pyrrolidinecarboxylate;

3-(3-pyridyl)-1-propyl (2S)-1-(2-cyclohexyl-1,2-dioxoethyl)-2-pyrrolidinecarboxylate;

3-(3-pyridyl)-1-propyl (2S)-N-( [2-thienyl]glyoxyl) pyrrolidinecarboxylate;

3,3-diphenyl-1-propyl (2S)-1-(3,3-dimethyl-1,2-dioxobutyl)-2-pyrrolidinecarboxylate;

3,3-diphenyl-1-propyl (2S)-1-cyclohexylglyoxyl-2-pyrrolidinecarboxylate; and 3,3-diphenyl-1-propyl (2S)-1-(2-thienyl)glyoxyl-2-pyrrolidinecarboxylate;

or a pharmaceutically acceptable salt, ester, or solvate thereof.

14. The method of claim 13, wherein the compound is selected from the group consisting of:

3-(3-pyridyl)-1-propyl (2S)-1-(3,3-dimethyl-1,2-dioxopentyl)-2-pyrrolidinecarboxylate;

3-(2-pyridyl)-1-propyl (2S)-1-(3,3-dimethyl-1,2-dioxopentyl)-2-pyrrolidinecarboxylate; and 3-(3-pyridyl)-1-propyl (2S)-1-(2-cyclohexyl-1,2-dioxoethyl)-2-pyrrolidinecarboxylate;

or a pharmaceutically acceptable salt, ester, or solvate thereof.

15. The method of claim 14, wherein the compound is 3-(3-pyridyl)-1-propyl (2S)-1-(3,3-dimethyl-1,2-dioxopentyl)-2-pyrrolidinecarboxylate, or a pharmaceutically acceptable salt, ester, or solvate or hydrate thereof.

16. The method of claim 1, wherein the compound is an N-glyoxyl prolyl ester.

* * * * *